(12) United States Patent
Jimenez et al.

(10) Patent No.: US 8,242,272 B2
(45) Date of Patent: Aug. 14, 2012

(54) PROCESS FOR PREPARING 5-FLUORO-1H-PYRAZOLO [3,4-B] PYRIDIN-3-AMINE AND DERIVATIVES THEREOF

(75) Inventors: Juan Miguel Jimenez, Abingdon (GB); Philip Collier, Abingdon (GB); Andrew Miller, Upton (GB); Jeremy Green, Waltham, MA (US); Huai Gao, Arlington, MA (US); Sylvain Loïc Jean-Luc Hamon, Groningen (NL); Albert Cornelis Dros, Groningen (NL)

(73) Assignee: Vertex Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 12/695,292

(22) Filed: Jan. 28, 2010

(65) Prior Publication Data

US 2010/0184980 A1    Jul. 22, 2010

Related U.S. Application Data

(63) Continuation of application No. PCT/US2008/071714, filed on Jul. 31, 2008.

(60) Provisional application No. 60/953,019, filed on Jul. 31, 2007.

(51) Int. Cl.
C07D 471/04 (2006.01)
(52) U.S. Cl. .................................. 544/328; 546/119
(58) Field of Classification Search ............... 544/328; 546/119
See application file for complete search history.

(56) References Cited

U.S. PATENT DOCUMENTS

| | | | |
|---|---|---|---|
| 6,653,300 B2 | 11/2003 | Bebbington et al. |
| 6,689,778 B2 | 2/2004 | Bemis et al. |
| 6,825,190 B2 | 11/2004 | Moon et al. |
| 6,884,804 B2 | 4/2005 | Choon-Moon |
| 7,008,948 B2 | 3/2006 | Bebbington et al. |
| 7,304,061 B2 | 12/2007 | Hale et al. |
| 7,345,054 B2 | 3/2008 | Hale et al. |
| 7,361,665 B2 | 4/2008 | Ledeboer et al. |
| 7,390,815 B2 | 6/2008 | Davies et al. |
| 7,427,681 B2 | 9/2008 | Bebbington et al. |
| 7,473,691 B2 | 1/2009 | Davies et al. |
| 7,491,730 B2 | 2/2009 | Forster et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,579,349 B2 | 8/2009 | Nowak et al. |
| 7,625,913 B2 | 12/2009 | Bebbington et al. |
| 7,691,853 B2 | 4/2010 | Bebbington et al. |
| 7,737,151 B2 | 6/2010 | Mortimore et al. |
| 7,767,672 B2 | 8/2010 | Binch et al. |
| 7,820,685 B2 | 10/2010 | Binch et al. |
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 2003/0096813 A1 | 5/2003 | Cao et al. |
| 2003/0105090 A1 | 6/2003 | Bebbington et al. |
| 2003/0199526 A1 | 10/2003 | Choquette et al. |
| 2003/0207873 A1 | 11/2003 | Harrington |
| 2004/0009981 A1 | 1/2004 | Bebbington et al. |
| 2004/0049032 A1 | 3/2004 | Charrier et al. |
| 2004/0157893 A1 | 8/2004 | Bebbington et al. |
| 2005/0049246 A1 | 3/2005 | Bemis et al. |
| 2005/0228005 A1 | 10/2005 | Moon et al. |
| 2007/0179125 A1 | 8/2007 | Fraysse et al. |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0267628 A1 | 10/2010 | O'Harte et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0269732 A1 | 11/2011 | Golec et al. |

FOREIGN PATENT DOCUMENTS

WO    9838171    9/1998
(Continued)

OTHER PUBLICATIONS

Jambhekar, S.S., "Biopharmaceutical Properties of Drug Substances" in Principles of Medicinal Chemistry, 4th ed., 12-24, (1995).
Layzer, R.B., "Section Five—Degenerative Diseases of the Nervous System" in Cecil Textbook of Medicine, 20th ed., 2: 2050-2057 (1996).
Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).
Medwid, J.B. et al., "Preparation of Triazolo[ 1,5-c]pyrimidines as Potential Antiasthma Agents," J. Med. Chem. 33, 1230-1241 (1990).
Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

(Continued)

*Primary Examiner* — Deepak Rao
(74) *Attorney, Agent, or Firm* — Rory C. Stewart

(57) ABSTRACT

The present invention relates to a process for the synthesis of 5-fluoro-1H-pyrazolo[3,4-b]pyridin-3-amine in high yield and purity. The present invention also relates to processes for the synthesis of 5-fluoro-1H-pyrazolo[3,4-b]pyridin-3-amine derivatives. These processes are useful for preparing biologically active compounds, particularly certain GSK-3 inhibitors, or derivatives thereof.

25 Claims, No Drawings

FOREIGN PATENT DOCUMENTS

| | | |
|---|---|---|
| WO | 0021955 | 4/2000 |
| WO | 0174768 | 11/2001 |
| WO | 0222602 | 3/2002 |
| WO | 03078426 | 9/2003 |
| WO | WO 2004/013140 * | 2/2004 |
| WO | 2007023382 | 1/2007 |
| WO | 2007059299 | 5/2007 |
| WO | 2008057940 | 5/2008 |
| WO | WO 2008/057940 * | 5/2008 |

OTHER PUBLICATIONS

Cohen, P., "Dissection of the Protein Phosphorylation Cascades Involved in Insulin and Growth Factor Action", Biochem. Soc. Trans., 21, 555-567 (1993).

Haq, S. et al., "Glycogen Synthase Kinase-3β Is a Negative Regulator of Cardiomyocyte Hypertrophy", J. Cell Biol., 151(1), 117-129 (2000).

Fischer, P.M. et al., "Inhibitors of Cyclin-Dependent Kinases as Anti-Cancer Therapeutics", Current Med. Chem., 7, 1213-1245 (2000).

Mani, S. et al., "Cyclin-dependent kinase: novel anticancer agents", Exp. Opin. Invest. Drugs., 8, 1849-1870 (2000).

Fry, D.W. et al., "Inhibitors of cyclin-dependent kinases as therapeutic agents for the treatment of cancer", Current Opin. Oncol. Endoc. & Metab. Investig., 2-40-59 (2000).

Bokemeyer, D. et al., "Multiple intracellular MAP kinase signaling cascades", Kidney Int., 49, 1187-1198 (1996).

Anderson, N. G. et al., "Multiple intracellular MAP kinase signaling cascades", Nature, 343, 651-653 (1990).

Crews, C.M. et al., "The Primary Structure of MEK, a Protein Kinase That Phosphorylates the ERK Gene Product", Science, 258, 478-480 (1992).

Bjorbaek, C. et al, "Divergent Functional Roles for p90rsk Kinase Domains", J. Biol. Chem., 270(32), 18848-18552 (1995).

Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).

Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).

Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).

Moodie, S.A. et al., "Complexes of Ras-GTP with Raf-1 and Mitogen-Activated Protein Kinase Kinase", Science, 260 (5114), 1658-1661 (1993).

Frey, R.S. et al., "Involvement of Extracellular Signal-regulated Kinase 2 and Stress-activated Protein Kinase/Jun N-Terminal Kinase Activation by Transforming Growth Factor (3 in the Negative Growth Control of Breast Cancer Cells", Cancer Res., 57, 628-633 (1997).

Sivaraman, V.S., et al., "Hyperexpression of Mitogen-activated Protein Kinase in Human Breast Cancer", J. Clin. Invest., 99(7), 1478-1483 (1997).

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).

Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).

Kazuhiko, N. et al., "Akt/Protein Kinase B Prevents Injury-Induced Motoneuron Death and Accelerates Axonal Regeneration", J. of Neuroscience, 20(8), 2875-2986 (2000).

Molina, T.J. et al., "Profound block in thymocyte development in mice lacking p56lck", Nature, 357, 161-164 (1992).

Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).

Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).

Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).

Tanzi, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).

Charpiot, B. et al., "Quinazolines: Combined type 3 and 4 phosphodiesterase inhibitors", Bioorg. Med. Chem. Lett., 8 (20), 2891-2896 (1998).

Shikhaliev, K.S. et al., "Heterocyclization of quinazol-2-ylguanidines. 1. Reaction with amino acids", Chem. Heterocycl. Compd., 35 (7), 818-820 (1999).

Singh, S.P. et al., "Synthesis & Mass Spectra of Some Substituted 2-(2'-Benzazolylamino)pyrimidines", Indian J. Chem. Sect. B, 22(1); 37-42 (1983).

Ti, J. et al., "Anticandidal activity of pyrimidine-peptide conjugates", J. Med. Chem., 23(8), 913-918 (1980).

Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).

Myers, M.R. et al., "The synthesis and SAR of new 4-(N-alkyl-N-phenyl)amino-6,7-dimethoxyquinazolines and 4-(Nalkyl-N-phenyl)aminopyrazolo[3,4-d]pyrimidines, inhibitors of CSF-1R tyrosine kinase activity", Bioorg. Med. Chem. Lett., 7, 4, 421-424 (1997).

Agarwal, N. et al., "Suitably functionalised pyrimidines as potential antimycotic agents", Bioorg. Med. Chem. Lett., 10, 8, 703-706 (2000).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Noell, C.W. et al., "Potential Purine Antagonists. XX. The Preparation and Reactions of Some Methylthiopurines", J. Am. Chem. Soc., 81(22), 5997-6007 (1959).

Lubbers, T. et al., "Design, synthesis, and structure—activity relationship studies of ATP analogues as DNA gyrase inhibitors", Bioorg. Med. Chem. Lett., 10, 8, 821-826 (2000).

D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f)quinozalines and their oxides", Indian J. Chem. Sect. B, 34, 9, 778-790 (1995).

Curd, F.H.S. et al, "Synthetic antimalarials. Part XVII. Some aminoalkylaminoquinoline derivatives", J. Chem. Soc., 899-909 (1947).

Haworth, R. D. et al., "Synthetic antimalarials. Part XXVII. Some derivatives of phthalazine, quinoxaline, and isoquinoline", J. Chem. Soc., 777-782 (1948).

Nair, M.D., et al., "3-Chloroisocarbostyril & Its Chlorination Products", Indian J. Chem., 467-470 (1967).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Gnecco, D. et al., "An Improved Preparation of 1-Methyl-4-Cyano-4-phenylpiperidine", Org. Prep. Proced. Int., 18 (4), 478-480 (1996).

Fedorynski, M. et al., "Synthesis of 1-Arycyclopropanecarbonitriles under Phase-transfer Catalytic Conditions", Org. Prep. Proced. Int, 27(3), 355-359 (1995).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Prasad, G. et al., "18-Crown-6 as a catalyst in the dialkylation of o-nitrophenacyl derivatives", J. Org. Chem., 25, 7188-7190 (1991).
Moss, R.A. et al., "Conversion of 'Obstinate' Nitriles to Amidines by Garigipati's Reaction", Tetrahedron Lett., 36(48), 8761-8764 (1995).
Garigipati, R.S., "An efficient conversion of nitriles to amidines", Tetrahedron Lett., 31(14), 1969-1972 (1990).
Warner, S.L. et al, "Targeting Aurora-2 Kinase in Cancer," Mol. Cancer Thera., 2, 589-585, 2003.
Wagman, A.S. et all, "Discovery and Development of GSK3 Inhibitors for the Treatment of Type 2 Diabetes," Current Pharmaceutical Design, 10, 1105-1137 (2004).
Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).
Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).
Soriano, P. et al., "Targeted Disruption of the C-SIC Pmto-Oncogene Leads to Osteopetrosis in Mice," Cell, 64: 693-702, (1991).
Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).
Casanova, B. et al., "Revisión crítica de la patogenia actual de la esclerosis multiple y futuras direcciones posibles," Rev. Neurol., 28 (9): 909-915 (1999).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Simone, J.V., "Oncology: Introduction" in Cecil Textbook in Medicine, 20th ed., vol. 1, 1004-1010 (1996).
Coleman, R.A., "The Biological Evaluation of New Compounds" in Medicinal Chemistry: Principles and Practice, King, Frank D. ed, Royal Society of Chemistry, 53-66 (1994).
The Condensed Chemical Dictionary, Sixth Edition by Arthur and Elizabeth Rose, 38 (1961).
Damasio, A.R., "Alzheimer's Disease and Related Dementia," in Cecil Textbook of Medicine, 20th ed., 2: 1992-1996 (1996).
Rogers, E. et al., "The aurora kinase AIR-2 functions in the release of chromosome cohesion in Caenorhabditis elegans meiosis," J. Cell Biol., 157(2): 219-229 (2002).
Fisher A., "Therapeutic Strategies in Alzheimer's Disease: M1 Muscarinic Agonists," Jpn. J. Pharmacol., 84(2):101-12 (2000).
Frame, M.C., "Src in cancer: deregulation and consequences for cell behaviour," Biochimica et Biophysica Acta., 1602, 114-130 (2002).
Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).
Ganellin, C.R., "Past Approaches to Discovering New Drugs as Medicines" in Medicinal Chemistry, Principles and Practices. King, Frank D. ed, Royal Society of Chemistry, 189-205 (1994).
Hamdane, M. et al., "A Therapeutic Target in Alzheimer Neurodegeneration," J. Mol. Neurosci., 19(3): 275-87 (2002).
Hardt, S.E. et al., "Glycogen Synthase Kinase-3β—A Novel Regulator of Cardiac Hypertrophy and Development," Circulation Research, 90: 1055-1063 (2002).
Parnell, E.W., "2-Cyano-4-nitrophenylhydrazine and 3-Amino-5-nitroindazole", J. Chem. Soc., 2363-2365 (1959).
Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).
Hendriksen, E.J. et al., "Modulation of muscle insulin resistance by selective inhibition of GSK-3 in Zucker diabetic fatty rats," Am. J. Physiol. Endocrinol. Metab., 284: E892-E900 (2003).
Okafor, C.O., "Studies in the Heterocyclic Series. X. 1,3,9-Triazaphenothiazine Ring System, a New Phenothiazine Ring," J. Org. Chem., 40(19): 2753-2755 (1975).
U.S. Appl. No. 12/433,998, filed May 1, 2009.
U.S. Appl. No. 12/486,235, filed Jun. 17, 2009.
U.S. Appl. No. 12/791,976, filed Jun. 2, 2010.
U.S. Appl. No. 12/792,044, filed Jun. 2, 2010.
U.S. Appl. No. 12/792,050, filed Jun. 2, 2010.
U.S. Appl. No. 12/436,407, filed May 6, 2009.
U.S. Appl. No. 11/600,588, filed Nov. 16, 2006.
U.S. Appl. No. 12/562,181, filed Sep. 18, 2009.
U.S. Appl. No. 12/598,275, filed Oct. 30, 2009.
U.S. Appl. No. 12/595,703, filed Oct. 13, 2009.
U.S. Appl. No. 12/595,878, filed Oct. 14, 2009.
U.S. Appl. No. 12/598,276, filed Oct. 30, 2009.
U.S. Appl. No. 12/598,277, filed Oct. 30, 2009.
U.S. Appl. No. 12/601,026, filed Nov. 20, 2009.
U.S. Appl. No. 10/728,113, filed Dec. 4, 2003.
U.S. Appl. No. 10/999,128, filed Nov. 29, 2009.
U.S. Appl. No. 10/125,885, filed Apr. 19, 2002.
U.S. Appl. No. 10/119,890, filed Apr. 10, 2002.
U.S. Appl. No. 12/127,530, filed May 27, 2008.
U.S. Appl. No. 12/651,839, filed Jan. 4, 2010.
U.S. Appl. No. 13/094,183, filed Apr. 26, 2011.
U.S. Appl. No. 10/026,966, filed Dec. 19, 2001.
U.S. Appl. No. 10/722,374, filed Nov. 25, 2003.
U.S. Appl. No. 12/109,598, filed Apr. 25, 2008.
U.S. Appl. No. 12/967,675, filed Dec. 14, 2010.
U.S. Appl. No. 10/389,259, filed Mar. 14, 2003.
U.S. Appl. No. 10/464,430, filed Jun. 18, 2003.
U.S. Appl. No. 11/786,150, filed Apr. 11, 2007.
U.S. Appl. No. 10/314,905, filed Dec. 9, 2002.
U.S. Appl. No. 11/803,878, filed May 16, 2007.
U.S. Appl. No. 12/410,553, filed Mar. 25, 2009.
U.S. Appl. No. 12/796,297, filed Jun. 8, 2010.
U.S. Appl. No. 12/894,465, filed Sep. 30, 2010.
U.S. Appl. No. 13/309,970, filed Dec. 2, 2011.

* cited by examiner

PROCESS FOR PREPARING 5-FLUORO-1H-PYRAZOLO [3,4-B] PYRIDIN-3-AMINE AND DERIVATIVES THEREOF

CROSS REFERENCE TO RELATED APPLICATIONS

This present application is a continuation of International Application No. PCT/US2008/071714, filed on Jul. 31, 2008, which claims the benefit, under 35 U.S.C. §119, to U.S. Provisional Application No. 60/953,019, filed on Jul. 31, 2007, the entire contents of each application being incorporated herein by reference.

TECHNICAL FIELD OF THE INVENTION

The present invention relates to a process for the synthesis of 5-fluoro-1H-pyrazolo[3,4-b]pyridin-3-amine in high yield and purity. The present invention also relates to a process for the synthesis of 5-fluoro-1H-pyrazolo[3,4-b]pyridin-3-amine derivatives. The process is useful for preparing biologically active compounds, particularly certain GSK-3 inhibitors, or derivatives thereof.

BACKGROUND OF THE INVENTION 5-fluoro-1H-pyrazolo[3,4-b]pyridin-3-amine derivatives are known to be GSK-3 inhibitors (WO2004/013140).

Previous attempts at large scale production of 2-chloro-5-fluoronicotinamide, one of the key intermediates of the synthesis of 5-fluoro-1H-pyrazolo[3,4-b]pyridin-3-amine, was not reproducible due to the large amounts of catalyst and hydrogen gas required. Moreover, large scale synthesis of the intermediate resulted in a mixture of starting material and product, which required separation.

Accordingly, the need exists for a process for the facile synthesis of 5-fluoro-1H-pyrazolo[3,4-b]pyridin-3-amine to obtain 5-fluoro-1H-pyrazolo[3,4-b]pyridin-3-amine derivatives in high yield and purity.

SUMMARY OF THE INVENTION

The present invention provides a process for preparing a compound of formula 5:

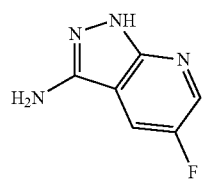

comprising:
1) selectively de-chlorinating a compound of formula 1

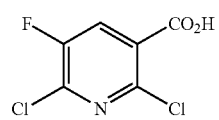

under suitable de-chlorination conditions to form a compound of formula 2:

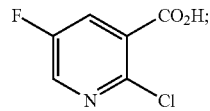

2) treating the compound of formula 2 with suitable amide formation conditions to form a compound of formula 3:

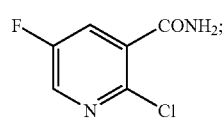

3) reducing the compound of formula 3 under suitable reduction conditions to form a compound of formula 4:

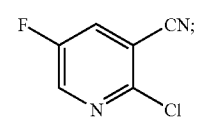

4) cyclizing a compound of formula 4 with $H_2NNH_2 \cdot H_2O$ under suitable cyclization conditions to form the compound of formula 5.

The present invention also provides a process for making a compound of formula I:

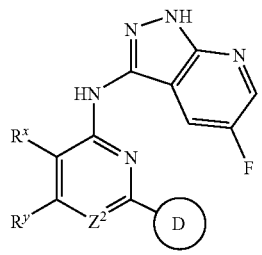

Wherein $R^x$, $R^y$, $Z^2$ and Ring D are as defined herein. The processes of this invention comprise the step of synthesizing a compound of formula 5 and combining it with a compound of formula 6:

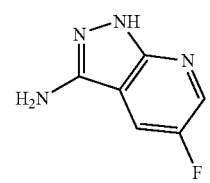

-continued

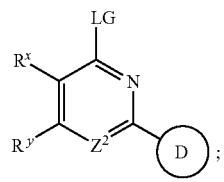

wherein $R^x$, $R^y$, $Z^2$ and Ring D are as defined herein and LG is a suitable leaving group; under suitable reaction conditions to form a compound of formula I.

The processes of this invention have the advantage of allowing preparation of compounds of formula I in high yield and purity, a preparation that is readily scaled up for large scale preparation.

These compounds of formula I are particularly useful as GSK-3 inhibitors. These compounds and pharmaceutically acceptable compositions thereof are also useful for treating or preventing a variety of diseases, disorders or conditions, including, but not limited to, an autoimmune, inflammatory, proliferative, or hyperproliferative disease, a neurodegenerative disease, or an immunologically-mediated disease.

DETAILED DESCRIPTION OF THE INVENTION

One aspect of the invention provides a process for preparing a compound of formula 5:

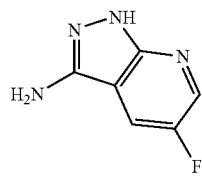

comprising the step of:
1) selectively de-chlorinating a compound of formula 1

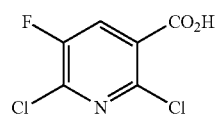

under suitable de-chlorination conditions to form a compound of formula 2:

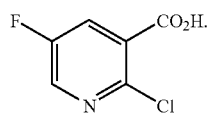

Another embodiment further comprises the step of treating the compound of formula 2 with suitable amide formation conditions to form a compound of formula 3:

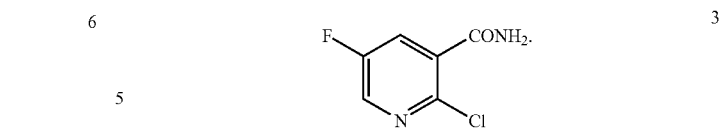

Another embodiment further comprises the step of reducing the compound of formula 3 under suitable reduction conditions to form a compound of formula 4:

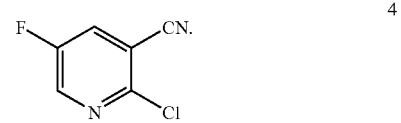

Yet another embodiment further comprises the step of cyclizing a compound of formula 4 with $H_2NNH_2.H_2O$ under suitable cyclization conditions to form the compound of formula 5.

De-Chlorination Conditions

In one embodiment, the de-chlorination conditions comprise adding a palladium catalyst (such as $Pd(OAc)_2$), $PPh_3$, a suitable base (such as $Et_3N$), and a suitable acid (such as formic acid HCOOH). In some embodiments, this reaction is done in DMF under $N_2$ atmosphere. The reaction can be monitored by analysis of aliquots taken from the reaction mixture, such as with $^1HNMR$ analysis. In some embodiments, if the reaction is incomplete, more catalyst and $HCOOH/Et^3N$ can be added and the reaction can be stirred for longer. In some embodiments, the reaction is done at a temperature below 60° C. In some embodiments, at 50° C. In some embodiments, the reaction mixture, upon completion, is cooled to about 0° C., to which water is added. In some embodiments, the reaction mixture is then filtered through celite. The reaction mixture is basified to pH 9 (using a base such as 30% aq NaOH) and is subsequently washed with an organic solvent (such as EtOAc). The mixture is then acidified to pH 1 (using an acid such as 12N HCl) and the mixture is then washed with sat. NaCl. In some embodiments, the organic phase is concentrated under reduced pressure to give 88% yield of a beige solid which can be used in the next step without further purification.

Amide Formation Conditions

Suitable amide formation conditions from a carboxylic acid are known to those skilled in the art. In one embodiment, the amide formation condition comprises a two-step process. In the first step, an acid chloride is generated (formula 2-1). In the second step, ammonia ($NH_3$) is added.

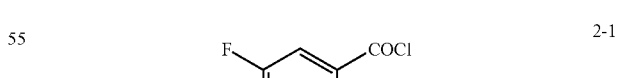

Acid chlorides can be formed from carboxylic acids via a variety of reagents that are known to one of skill in the art. Examples of such reagents include, but are not limited to, oxalyl chloride and thionyl chloride. In some embodiments, such chlorination reactions are done in the presence of DMF and DCM. In some embodiments, a solution of the carboxylic acid is cooled in a solution of DMF and DCM to about 0° C.

before the chlorinating reagent is added. In some embodiments, the resultant reaction mixture is stirred at room temperature until the reaction has gone to completion. In some embodiments, the resultant reaction mixture is concentrated in vacuo to form the acid chloride.

In the second step, ammonia is typically bubbled into a solution that contains the acid chloride and a suitable solvent. Suitable solvents include, but are not limited to, aprotic solvents. An aprotic solvent is a solvent which cannot donate a hydrogen bond. Examples of aprotic solvents include dioxane, tetrahydrofuran, ether, $CH_2Cl_2$, and chloroform.

Reduction Conditions

Suitable reduction conditions are known to one of skill in the art. In one embodiment, the reduction conditions comprise adding TFAA dropwise to a cooled (e.g., 0° C.) suspension of the 2-chloro-5-fluoronicotinamide, $Et_3N$ and DCM. The reaction mixture is stirred for about 90 minutes at 0° C. Upon completion, the reaction mixture is diluted with a suitable solvent (e.g., DCM), washed with sat. aq. $NaHCO_3$ and brine, and dried with a suitable drying agent (e.g., $Na_2SO_4$, $MgSO_4$). The organic layer is filtered and concentrated to provide the desired compound. In some embodiments, the desired compound is purified via column chromatography.

Suitable Cyclization Conditions

Suitable cyclization conditions are known to one of skill in the art. In one embodiment, 2-Chloro-5-fluoronicotinonitrile is refluxed with hydrazine monohydrate in butanol. In some embodiments, said reaction is refluxed for about 4 hours. The mixture is then cooled to room temperature and concentrated. The precipitate can then be successively washed on filter with water, $Et_2O$, and dried in vacuo overnight to provide the desired compound.

The compound of formula 5 may be used to prepare compounds of formula I as described herein.

Another embodiment provides a process for preparing a compound of formula I:

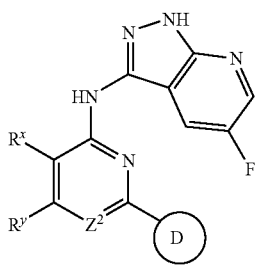

I wherein
$Z^2$ is N or $CR^z$;
$R^x$ is $T^1$-$R^3$;
$R^y$ is $T^2$-$R^{10}$; or
$R^x$ and $R^y$ are taken together with their intervening atoms to form a fused aromatic or non-aromatic 5-8 membered ring having 0-3 ring heteroatoms selected from oxygen, sulfur, or nitrogen, wherein any substitutable carbon on said fused ring formed by $R^x$ and $R^y$ is substituted by T-$R^3$, and any substitutable nitrogen on said ring formed by $R^x$ and $R^y$ is substituted by $R^4$;
$R^z$ is H, halo, or $C_{1-6}$ aliphatic, wherein the aliphatic is optionally substituted with 1-5 groups selected from halo, —CN, and —OR;
each T and $T^1$ is independently a bond or a $C_{1-4}$ alkylidene chain;

$T^2$ is independently a bond or a $C_{1-4}$ alkylidene chain wherein up to three methylene units of the alkylidene chain are optionally replaced by —O—; —C(=O)—, —S(O)—, —S(O)$_2$—, —S—, or —N($R^4$)—;

Ring D is a 4-7 membered monocyclic ring or 8-10 membered bicyclic ring selected from a heterocyclyl, aryl, heteroaryl, or carbocyclyl ring; said heterocyclyl or heteroaryl ring having 1-4 ring heteroatoms selected from nitrogen, oxygen or sulfur, wherein each substitutable ring carbon of Ring D is independently substituted with oxo, or —$R^5$ and any substitutable ring nitrogen is independently substituted with —$R^4$;

$R^1$ is selected from -halo, —CN, —NO$_2$, T-V—$R^6$, phenyl, 5-6 membered heteroaryl ring, 5-6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring D;

V is —O—, —S—, —SO—, —SO$_2$—, —N($R^6$) SO$_2$—, —SO$_2$N($R^6$)—, —N($R^6$)—, —CO—, —CO$_2$—, —N($R^6$) CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)$_2$N($R^6$)CON($R^6$)—;

each $R^3$ and $R^{10}$ is independently selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$R", —N($R^4$)N($R^4$)$_2$, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5-10 ring atoms, or a heterocyclyl ring having 4-10 ring atoms; each R is optionally substituted with 0-5 $R^9$ or J;

each $R^4$ is independently selected from —$R^7$, —COR$^7$, —CO$_2$R", —CON($R^7$)$_2$, or —SO$_2$R$^7$, or two $R^4$ on the same nitrogen are taken together to form a 3-8 membered heterocyclyl or heteroaryl ring; wherein said heterocyclyl or heteroaryl ring is optionally substituted by 0-3 $J^4$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$R", —N($R^4$)N($R^4$)$_2$, —C(=NH)N($R^4$)$_2$, —C(=NH)—OR, —N($R^4$)CON($R^4$)$_2$, —N($R^4$)SO$_2$N($R^4$)$_2$, —N($R^4$)SO$_2$R, or —OC(=O)N($R^4$)$_2$;

each $R^6$ is independently selected from hydrogen or $C_{1-4}$ aliphatic group optionally substituted with 0-3 $J^6$; or two $R^6$ groups on the same nitrogen atom are taken together with the nitrogen atom to form a 5-6 membered heterocyclyl or heteroaryl ring, wherein said heterocyclyl or heteroaryl ring is optionally substituted with 0-4 $J^6$;

each $R^7$ is independently selected from hydrogen or R"; or two $R^7$ on the same nitrogen are taken together with the nitrogen to form a 5-8 membered heterocyclyl or heteroaryl ring, wherein said heterocyclyl or heteroaryl ring is optionally substituted with 0-4 J";

each $R^8$ is independently selected from —$OR^6$, —$SR^6$, —$COR^6$, —$SO_2R^6$, —$N(R^6)_2$, —$N(R^6)N(R^6)_2$, —CN, —$NO_2$, —$CON(R^6)_2$, —$CO_2R^6$, or a $C_{1-4}$ aliphatic group, wherein said $C_{1-4}$ aliphatic group is optionally substituted with 0-3 $J^8$;

each $R^9$ is —R', -halo, —OR', —C(=O)R', —$CO_2$R', —COCOR', $COCH_2$COR', —$NO_2$, —CN, —S(O)R', —$S(O)_2$R', —SR', —N(R')$_2$, —CON(R')$_2$, —$SO_2$N(R')$_2$, —OC(=O)R', —N(R')COR', —N(R')$CO_2$($C_{1-6}$ aliphatic), —N(R')N(R')$_2$, —N(R')CON(R')$_2$, —N(R')$SO_2$N(R')$_2$, —N(R')$SO_2$R', —OC(=O)N(R')$_2$, =NN(R')$_2$, =N—OR', or =O;

each R' is independently hydrogen or a $C_{1-6}$ aliphatic group optionally substituted with 0-4 J'; or two R', together with the atom(s) to which they are attached, form a 3-6 membered carbocyclyl or heterocyclyl wherein said carbocyclyl or heterocyclyl is optionally substituted with 0-4 J' and wherein said heterocyclyl contains 1-2 heteroatoms selected from O, N, or S;

each R" is independently $C_{1-6}$ aliphatic optionally substituted with 0-4 J"; and each $J^4$, J', and J" is independently $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo$C_{1-4}$ aliphatic), or halo$C_{1-4}$ aliphatic;

each J is halo, OH, or $C_{1-6}$ aliphatic;

each $J^6$ and $J^8$ is independently -halo, —OR, oxo, $C_{1-6}$ aliphatic, —C(=O)R, —$CO_2$R, —COCOR, $COCH_2$COR, —$NO_2$, —CN, —S(O)R, —$S(O)_2$R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$aliphatic), —N($R^4$)N($R^4$)$_2$, =NN($R^4$)$_2$, =N—OR, —N($R^7$)CON($R^7$)$_2$, —N($R^7$)$SO_2$N($R^7$)$_2$, —N($R^4$)$SO_2$R, or —OC(=O)N($R^7$)$_2$; or 2 $J^6$ or $J^8$ groups, on the same atom or on different atoms, together with the atom(s) to which they are bound, form a 3-8 membered saturated, partially saturated, or unsaturated ring having 0-2 heteroatoms selected from O, N, or S;

comprising the step of synthesizing a compound of formula 5 and combining it with a compound of formula 6:

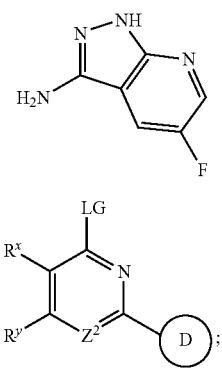

wherein LG is a suitable leaving group; and $R^x$, $R^y$, $Z^2$, and Ring D are as defined herein for compounds of formula I; under suitable reaction conditions to form a compound of formula I.

In some embodiments, said Ring D has one or two ortho substituents independently selected from —$R^1$, any substitutable non-ortho carbon position on Ring D is independently substituted by —$R^5$.

Another embodiment provides a process for preparing a compound of formula I:

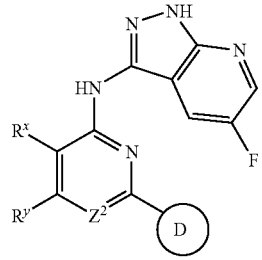

comprising the step of synthesizing a compound of formula 5 and combining it with a compound of formula 6:

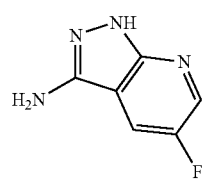

wherein LG is a suitable leaving group; and $R^x$, $R^y$, $Z^2$, and Ring D are as defined below for compounds of formula I; under suitable reaction conditions to form a compound of formula I; wherein $Z^2$ is N or CR$^z$;

$R^x$ is $T^1$-$R^3$;

$R^y$ is $T^2$-$R^{10}$; or $R^x$ and $R^y$ are taken together with their intervening atoms to form a fused aromatic or non-aromatic 5-8 membered ring having 0-3 ring heteroatoms selected from oxygen, sulfur, or nitrogen, wherein any substitutable carbon on said fused ring formed by $R^x$ and $R^y$ is substituted by T-$R^3$, and any substitutable nitrogen on said ring formed by $R^x$ and $R^y$ is substituted by $R^4$;

$R^z$ is H, halo, or $C_{1-6}$ aliphatic, wherein the aliphatic is optionally substituted with 1-5 groups selected from halo, —CN, and —OR;

each T and $T^1$ is independently a bond or a $C_{1-4}$ alkylidene chain;

$T^2$ is independently a bond or a $C_{1-4}$ alkylidene chain wherein up to three methylene units of the alkylidene chain are optionally replaced by —O—, —C(=O)—, —S(O)—, —$S(O)_2$—, —S—, or —N($R^4$)—;

Ring D is a 4-7 membered monocyclic ring or 8-10 membered bicyclic ring selected from a heterocyclyl, aryl, heteroaryl, or carbocyclyl ring; said heterocyclyl or heteroaryl ring having 1-4 ring heteroatoms selected from nitrogen, oxygen or sulfur, wherein each substitutable ring carbon of Ring D is independently substituted with oxo or —$R^5$ and any substitutable ring nitrogen is independently substituted with —$R^4$;

each $R^3$ and $R^{10}$ is independently selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$R", —N(R$^4$)N(R$^4$)$_2$, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is independently selected from hydrogen or an optionally substituted group selected from C$_{1-6}$aliphatic, C$_{6-10}$ aryl, a heteroaryl ring having 5-10 ring atoms, or a heterocyclyl ring having 4-10 ring atoms; each R is optionally substituted with 0-5 R$^9$;

each R$^4$ is independently selected from —R$^7$, —COR$^7$, —CO$_2$R", —CON(R$^7$)$_2$, or —SO$_2$R$^7$, or two R$^4$ on the same nitrogen are taken together to form a 3-8 membered heterocyclyl or heteroaryl ring;

each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$R", —N(R$^4$)N(R$^4$)$_2$, —C(=NH)N(R$^4$)$_2$, —C(=NH)—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

each R$^7$ is independently selected from hydrogen or R"; or two R$^7$ on the same nitrogen are taken together with the nitrogen to form a 5-8 membered heterocyclyl or heteroaryl ring, wherein said heterocyclyl or heteroaryl ring is optionally substituted with 0-4 J";

each R$^9$ is —R', -halo, —OR', —C(=O)R', —CO$_2$R', —COCOR', COCH$_2$COR', —NO$_2$, —CN, —S(O)R', —S(O)$_2$ R', —SR', —N(R')$_2$, —CON(R')$_2$, —SO$_2$N(R')$_2$, —OC(=O)R', —N(R')COR', —N(R')CO$_2$(C$_{1-6}$aliphatic), —N(R')N(R')$_2$, —N(R')CON(R')$_2$, —N(R')SO$_2$N(R')$_2$, —N(R')SO$_2$R', —OC(=O)N(R')$_2$, =NN(R')$_2$, =N—OR', or =O;

each R' is independently hydrogen or a C$_{1-6}$aliphatic group optionally substituted with 0-4 J'; or two R', together with the atom(s) to which they are attached, form a 3-6 membered carbocyclyl or heterocyclyl wherein said carbocyclyl or heterocyclyl is optionally substituted with 0-4 J' and wherein said heterocyclyl contains 1-2 heteroatoms selected from O, N, or S;

each R" is independently C$_{1-6}$aliphatic optionally substituted with 0-4 J"; and each J' and J" is independently NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic.

In some embodiments, the compound of formula 5 is synthesized according to the methods described herein.

In some embodiments, LG is selected from halogen groups (such as F, Cl, Br, or I); electronegative sulfonyl groups (such as arylsulfonyloxy, alkylsulfonyloxy, trifluoromethane-sulfonyloxy, alkylsulfonyl (such as methylsulfonyl), and alkylsulfoxide (such as methyl sulfoxide). In other embodiments, LG is halogen. In some embodiments, LG is chloro.

In some embodiments, Z$^2$ is N. In some embodiments, CR$^z$.

In some embodiments, the process is used to prepare a compound of one of the following formulae:

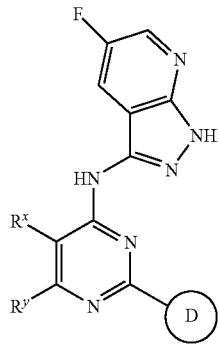

A-1

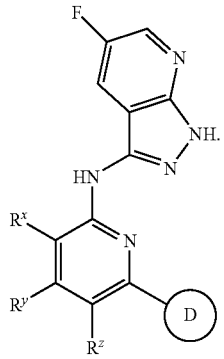

B-1

In some embodiments, Ring D is a 5-10 membered cycloaliphatic or a 5-10 membered heterocyclyl where said heterocyclyl contains 1-2 heteroatoms selected from O, N, or S; wherein the cycloaliphatic or heterocyclyl is optionally substituted with 1-5 —R$^5$. In some embodiments, 1-2 —R$^5$. In some embodiments, Ring D is bonded to the pyrimidine via a carbon atom. In some embodiments, said cycloaliphatic or heterocyclyl is optionally substituted with 1-2 —R$^5$ wherein —R$^5$ is halo or C$_{1-4}$alkyl. In some embodiments, —R$^5$ is fluoro or methyl.

In some embodiments, Ring D is a 4-7 membered monocyclic cycloaliphatic or heterocyclyl ring or an 8-10 membered bicyclic cycloaliphatic or heterocyclyl ring.

In other embodiments, Ring D is a 5-7 membered cycloaliphatic. In some embodiments, Ring D is cyclopropyl, cyclobutyl, cyclopentyl, cyclohexyl, or cycloheptyl, or adamantyl. In other embodiments, Ring D is a 5-7 membered heterocyclyl containing 1 heteroatom. In yet other embodiments, Ring D is a 6-membered heterocyclyl containing one oxygen atom. In some embodiments, Ring D contains at least one nitrogen atom. In some embodiments, Ring D is an optionally substituted ring selected from piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, or isoquinolinyl. In some embodiments, Ring D is optionally substituted tetrahydronaphthyl, benzodioxinyl, indanyl, indolinyl, or isoquinolinyl. In another embodiment, Ring D is tetrahydro-2H-pyran.

In another embodiment, Ring D is a 5-7 membered monocyclic aryl or heteroaryl ring, said heteroaryl ring having 1-4 ring heteroatoms selected from nitrogen, oxygen or sulfur. In some embodiments, Ring D is an optionally substituted ring selected from phenyl, pyridinyl, quinolinyl, or naphthyl. In other embodiments, Ring D is phenyl, pyridinyl, pyrimidinyl, pyridazinyl, pyrazinyl, or 1,2,4-triazinyl ring. In yet other embodiments, Ring D is phenyl or pyridinyl. In some other embodiments, Ring D is phenyl, imidazolyl, pyrazolyl, pyridyl, pyridazinyl, pyrazinyl, naphthyl, benzimidazolyl, benzthiazolyl, quinolinyl, quinazolinyl, isobenzofuran, indolyl, or indazolyl.

In some embodiments, Ring D is optionally substituted. In some embodiments, Ring D is phenyl, wherein the phenyl is optionally substituted with 1-5 —$R^5$.

In other embodiments, Ring D has one or two ortho substituents independently selected from —$R^1$; and any substitutable non-ortho carbon position on Ring D is independently substituted with —$R^5$. In yet other embodiments, two adjacent substituents on Ring D are optionally taken together with their intervening atoms to form a fused, unsaturated or partially unsaturated, 5-6 membered ring having 0-3 heteroatoms selected from oxygen, sulfur or nitrogen, wherein said fused ring is optionally substituted with halo, oxo, or —$R^8$.

In some embodiments, $R^1$ is selected from -halo, —CN, —$NO_2$, T-V—$R^6$, phenyl, 5-6 membered heteroaryl ring, 5-6 membered heterocyclyl ring, or a $C_{1-6}$aliphatic group; wherein said phenyl, heteroaryl, and heterocyclyl ring is each optionally substituted with up to three groups independently selected from halo, oxo, or —$R^8$; wherein said $C_{1-6}$aliphatic group is optionally substituted with halo, cyano, nitro, OH, or oxo. In other embodiments, $R^1$ and an adjacent substituent taken together with their intervening atoms form said ring fused to Ring D.

According to another embodiment, $R^1$ is -halo, an optionally substituted $C_{1-6}$aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —$OC(O)NH_2$, or —$NHSO_2R^6$. In some embodiments, $R^1$ is -halo, a $C_{1-6}$haloaliphatic group, an optionally substituted $C_{1-6}$aliphatic group, phenyl, or —CN. In other embodiments, $R^1$ is -halo, —CN, or a $C_{1-4}$aliphatic group optionally substituted with halogen. In some embodiments, $R^1$ is -halo; in some embodiments, chloro. In some embodiments, $R^1$ is chloro or $CF_3$. In some embodiments, $R^1$ is -halo, a $C_{1-6}$haloaliphatic group, an optionally substituted $C_{1-6}$aliphatic group, phenyl, or —CN and $R^y$ is azetidine. In some embodiments, said $C_{1-6}$aliphatic group is optionally substituted with halo.

In some embodiments, Ring D is a 3-8 membered cycloalkyl optionally substituted with 1-2 halo. In some embodiments, said halo is chloro or fluoro.

In some embodiments, each $R^6$ is independently selected from hydrogen or $C_{1-4}$aliphatic group optionally substituted with 0-3 $J^6$; or two $R^6$ groups on the same nitrogen atom are taken together with the nitrogen atom to form a 5-6 membered heterocyclyl or heteroaryl ring, wherein said heterocyclyl or heteroaryl ring is optionally substituted with 0-4 $J^6$.

In other embodiments, each $R^8$ is independently selected from —$OR^6$, —$SR^6$, —$COR^6$, —$SO_2R^6$, —$N(R^6)_2$, —$N(R^6)N(R^6)_2$, —CN, —$NO_2$, —$CON(R^6)_2$, —$CO_2R^6$, or a $C_{1-4}$aliphatic group, wherein said $C_{1-4}$aliphatic group is optionally substituted with 0-3 $J^8$.

In yet other embodiments, each $J^6$ and $J^8$ is independently -halo, —OR, oxo, $C_{1-6}$aliphatic, —C(=O)R, —$CO_2R$, —COCOR, —$COCH_2COR$, —$NO_2$, —CN, —S(O)R, —$S(O)_2$R, —SR, —$N(R^4)_2$, —$CON(R^7)_2$, —$SO_2N(R^7)_2$, —OC(=O)R, —$N(R^7)COR$, —$N(R^7)CO_2$ ($C_{1-6}$aliphatic), —$N(R^4)N(R^4)_2$, =$NN(R^4)_2$, =N—OR, —$N(R^7)CON(R^7)_2$, —$N(R^7)SO_2N(R^7)_2$, —$N(R^4)SO_2R$, or —$OC(=O)N$ $(R^7)_2$; or 2 $J^6$ or $J^8$ groups, on the same atom or on different atoms, together with the atom(s) to which they are bound, form a 3-8 membered saturated, partially saturated, or unsaturated ring having 0-2 heteroatoms selected from O, N, or S.

In some embodiments, $R^x$ is H or $C_{1-6}$aliphatic, wherein the aliphatic is optionally substituted with 1-5 halo. In other embodiments, $R^x$ is H or $C_{1-4}$ alkyl. In some embodiments, the alkyl is methyl, ethyl, cyclopropyl, or isopropyl. In some embodiments, the halo is fluoro. In yet other embodiments, $R^x$ is hydrogen, $C_{1-4}$aliphatic, or halo. In some embodiments, $R^x$ is hydrogen, fluoro, methyl, or ethyl. In other embodiments, $R^x$ is hydrogen.

In another embodiment, $R^Y$ is $T^2$-$R^{10}$ wherein $T^2$ is a bond. In some embodiments, $R^y$ is piperidinyl, piperazinyl, pyrrolidinyl, or morpholinyl.

In other embodiments, $R^y$ is $C_{1-4}$ alkyl optionally substituted with 0-2 $R^9$. In some embodiments, $R^9$ is OH or F. In some embodiments, $R^y$ is $CH_3$, $CF_3$, Cl, or $C(CH_3)_2OH$. In other embodiments, $R^y$ is halo; in some embodiments, chloro.

In other embodiments, $R^x$ and $R^y$ are both $O_{1-4}$ alkyl. In some embodiments, $R^x$ and $R^y$ are methyl. In other embodiments, $R^x$ is hydrogen and $R^y$ is not hydrogen. In some embodiments, $R^x$ is hydrogen and $R^Y$ is $T^2$-$R^{10}$ wherein $T^2$ is a bond, wherein $R^{10}$ is not hydrogen. In some embodiments, $R^x$ is hydrogen and $R^y$ is $CH_3$, $CF_3$, Cl, or $C(CH_3)_2OH$.

In other embodiments, $R^Y$ is represented by formula ii-a:

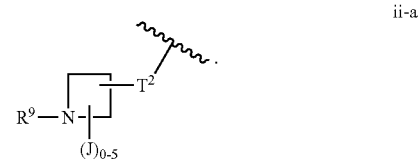

In some embodiments, $T^2$ is a bond. In some embodiments, $R^9$ is —$R^7$, —$COR^7$, —$CO_2R''$, —$CON(R^7)_2$, or —$SO_2R^7$.

In another embodiment, $R^Z$ is H or $C_{1-4}$ alkyl. In another embodiment, $R^Z$ is H or methyl. In some embodiments, $R^{10}$ is an optionally substituted azetidine. In another embodiment, $R^Y$ is represented by formula i:

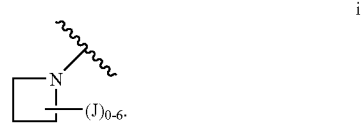

2. In yet another embodiment, $R^Y$ is represented by formula iii:

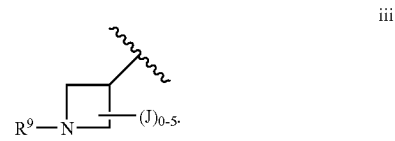

In some embodiments, $R^Y$ is azetidine and Ring D is an optionally substituted ring selected from phenyl, pyridinyl, pyrimidinyl, pyridazinyl, pyrazinyl, 1,2,4-triazinyl, imidazolyl, pyrazolyl, benzimidazolyl, benzthiazolyl, quinazolinyl, isobenzofuran, indolyl, indazolyl, quinolinyl, or naphthyl.

Another embodiment provides a process for preparing a compound of formula I wherein
$R^X$ is hydrogen or $C_{1-4}$aliphatic;
$R^Y$ is

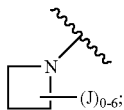

$C_{1-4}$alkyl optionally substituted with 0-2 J; or a 6 membered heterocyclyl containing 1-2 heteroatoms selected from O, N, or S;
J is halo, OH, or $C_{1-4}$aliphatic;
Ring D is phenyl, $C_{3-10}$cycloalkyl, or 5-7 membered heterocyclyl containing 1-2 heteroatoms selected from O, N, or S;
$R^1$ is $C_{1-4}$alkyl, $CF_3$, or halo;
$R^5$ is H; wherein the remaining variables are as defined herein.

Another embodiment provides a process for preparing a compound of formula I wherein
$R^X$ is hydrogen, methyl, or ethyl;
$R^Y$ is

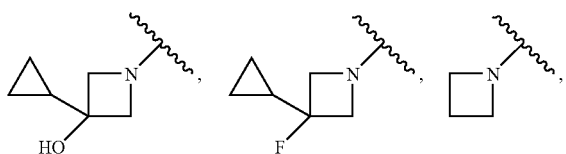

methyl, $CF_3$, Cl, morpholinyl, or $C(CH_3)_2OH$;
Ring D is phenyl, tetrahydro-2H-pyran, adamantyl, cyclopropyl, cyclobutyl, cyclopentyl, cyclohexyl, or cycloheptyl;
$R^1$ is methyl, $CF_3$, or halo;
$R^5$ is H;
wherein the remaining variables are as defined herein.

Another embodiment provides a process for preparing a compound of formula I wherein
$R^X$ is hydrogen or methyl;
$R^Y$ is methyl;
Ring D is phenyl or cyclohexyl;
$R^1$ is methyl, $CF_3$, or Cl;
$R^5$ is H;
wherein the remaining variables are as defined herein.

Schemes

Below are various schemes that show how to make compounds of this invention using the 5-fluoro-1H-pyrazolo[3,4-b]pyridin-3-amine intermediate.

Scheme I

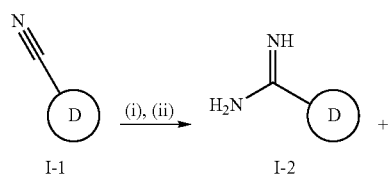

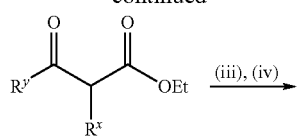

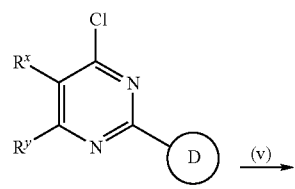

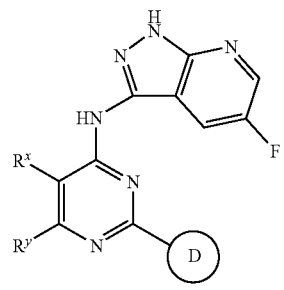

Reagents and conditions: (i) HCl, Et$_2$O/MeOH; (ii) NH$_3$, EtOH; (iii) Et$_3$N, EtOH, reflux; (iv) POCl$_3$, reflux; (v) 5-fluoro-1H-pyrazolo[3,4-b]pyridin-3-amine, DIPEA, NaI, DMF, 120° C.

Scheme I above shows a general synthetic route that is used for preparing the compounds I-5. Compounds of formula I-5 can be prepared from intermediate I-1. The formation of amidine I-2 is achieved by treating nitrile derivative I-1 with HCl in the presence of methanol and then treating the intermediate imidate with NH$_3$ in ethanol. Intermediate I-2 is then treated with the corresponding beta-ketoester via reflux in EtOH. The corresponding hydroxypyrimidine intermediate is treated with POCl$_3$ to yield chloroderivative I-4. This reaction is amenable to a variety of amidines (I-3). The chloropyrimidine I-4 is treated with 5-fluoro-1H-pyrazolo[3,4-b]pyridin-3-amine in the presence of DIPEA and NaI to yield the final compound I-5.

Scheme II

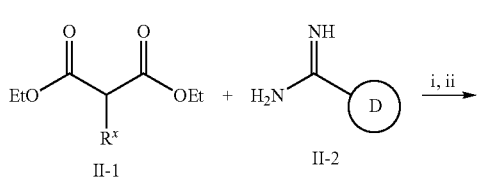

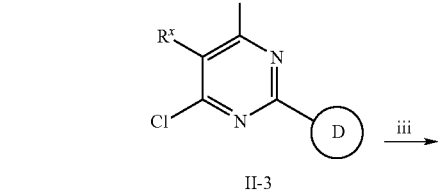

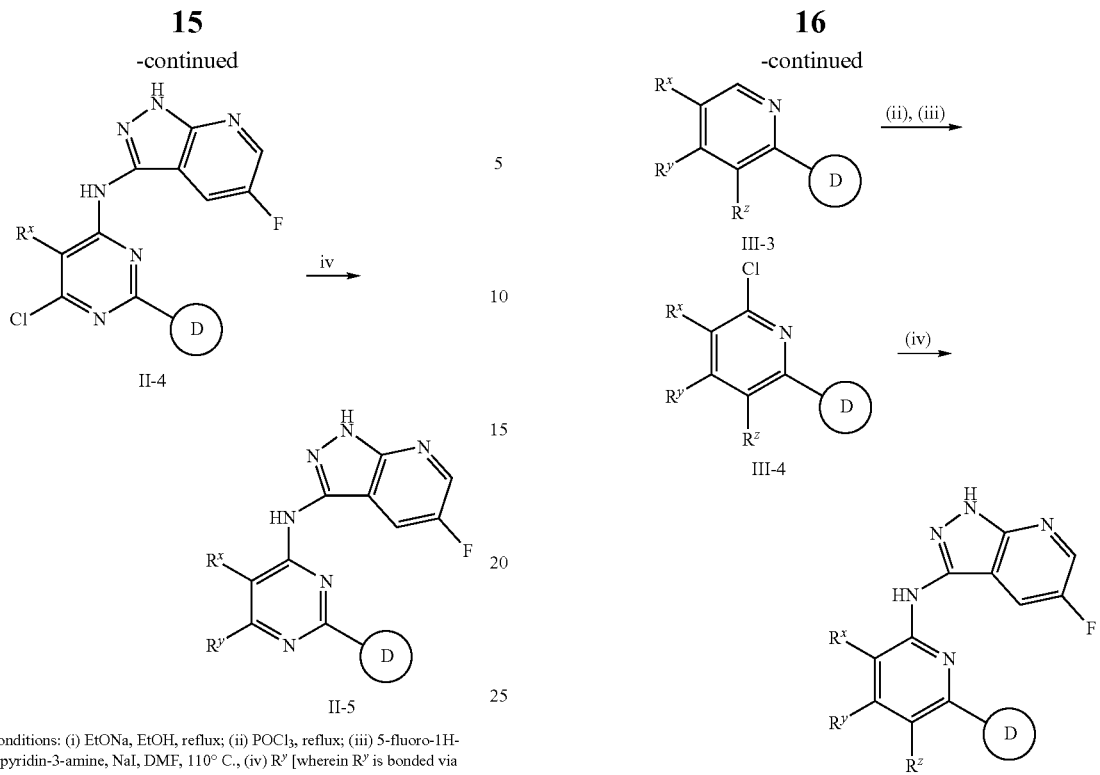

Reagents and conditions: (i) EtONa, EtOH, reflux; (ii) POCl₃, reflux; (iii) 5-fluoro-1H-pyrazolo[3,4-b]pyridin-3-amine, NaI, DMF, 110° C., (iv) Rʸ [wherein Rʸ is bonded via N-atom] n-butanol, 108° C.

Scheme II above shows a general synthetic route that is used for preparing the compounds II-5 wherein Rʸ is bonded to the pyrimidine via a nitrogen atom. Compounds of formula II-5 can be prepared from intermediate II-3. The formation of intermediate II-3 is achieved by reacting diethyl malonate (II-1) with the corresponding amidine (II-2) in the presence of EtONa as a base in refluxing ethanol. The crude is then treated with POCl₃ to yield dichloropyrimidine intermediate II-3. The dichloropyrimidine intermediate is sequentially treated with 1H-pyrazolo[3,4-b]pyridin-3-amine and Rʸ amine derivatives to yield final compounds II-5. These two reactions sequence are amenable to a variety of amines (Rʸ), such as heterocyclic and alkyl amines.

Scheme III

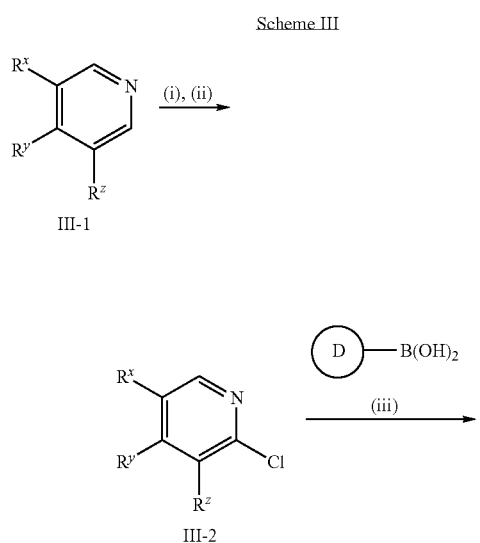

Reagents and conditions: (i) mCPBA, EtOAc; (ii) POCl₃; (iii) PdPPh₃)₂Cl₂, Ba(OH)₂, DME-H₂O, 110° C.; (iv) 5-fluoro-1H-pyrazolo[3,4-b]pyridin-3-amine, Pd(OAc)₂, Xantphos, K₂CO₃, dioxane, 120° C.

Scheme III above shows a general synthetic route that is used for preparing the compounds III-5. Compounds of formula III-5 can be prepared from intermediate III-1. The formation of chloropyridine derivative III-2 is achieved by treating the corresponding pyridine III-1 with m-CPBA in EtOAc followed by conversion of the corresponding N-oxide to the chloropyridine by treating it with POCl₃. Intermediate III-2 is then reacted with the corresponding boronic acid derivative to yield compound III-3 using Suzuki coupling conditions well known for those skilled in the art. This reaction is amenable to a variety of boronic acid derivatives. The pyridine III-3 is then converted in a chloropyridine derivative III-4 using the same two step procedures as used in step 1, m-CPBA oxidation followed by POCl₃ treatment. Intermediate III-4 is then treated with 5-fluoro-1H-pyrazolo[3,4-b]pyridin-3-amine in the presence of Pd as a catalyst to yield the final compound III-5.

Scheme IV

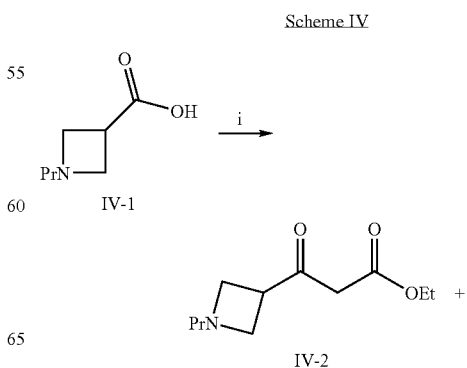

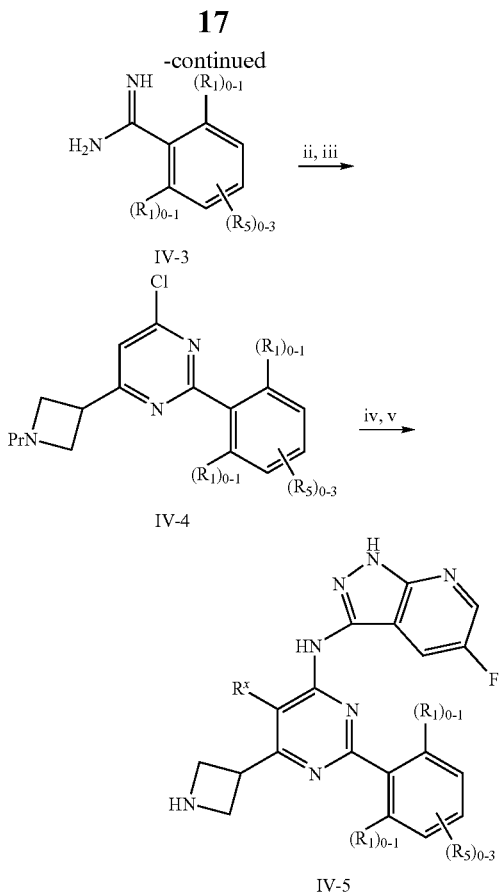

Reagents and conditions: (i) Meldrum's acid, DMAP, CDI, CH$_2$Cl$_2$ 0° C. to r.t., and then EtOH, reflux; (ii) Et$_3$N, EtOH, reflux; (iii) POCl$_3$, reflux; (iv) 5-fluoro-1H-pyrazolo[3,4-b]pyridin-3-amine, DIPEA, NaI, DMF, 120° C.; (v) TFA, DCM.

Scheme IV above shows a general synthetic route that is used for preparing the compounds of formula IV-5. Compounds of formula 5 can be prepared from intermediate IV-1. The formation of derivative IV-2 is achieved by treating intermediate IV-1 with Meldrum's acid in the presence of CDI, after coupling and decarboxylation the resulting acid is esterified by treating the crude mixture with refluxing ethanol. Intermediate IV-2 is then treated with amidine under reflux in EtOH and the corresponding hydroxypyrimidine intermediate is treated with POCl$_3$ to yield intermediate IV-4. This reaction is amenable to a variety of amidines IV-3. The chloropyrimidine IV-4 is treated with 5-fluoro-1H-pyrazolo[3,4-b]pyridin-3-amine in the presence of DIPEA and NaI and finally treated with TFA to remove the protecting group to yield the final compound IV-5.

Other optionally substituted azetidines intermediates can be made according to the methods described in WO 2007/056221.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or cyclic, branched or unbranched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclopropyl, cyclobutyl, cyclopentyl, cyclohexyl, cycloheptyl, cyclopropenyl, and bridged systems, such as bicyclodecane or bicycloheptane.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, or phosphorus, (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, or tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired reactive sites in a multifunctional compound. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, one or more methylene units of an alkyl or aliphatic chain can be optionally replaced with another atom or group of atoms. Examples of such atoms or groups would include, but are not limited to, —NR—, —O—, —S—, —$CO_2$—, —OC(O)—, —C(O)CO—, —C(O)—, —C(O)NR—, —C(=N—CN), —NRCO—, —NRC(O)O—, —$SO_2$NR—, —$NRSO_2$—, —NRC(O)NR—, —OC(O)NR—, —$NRSO_2$NR—, —SO—, or —$SO_2$—, wherein R is defined herein. Unless otherwise specified, the optional replacements form a chemically stable compound. Optional replacements can occur both within the chain and at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a $C_3$aliphatic can be optionally replaced by —NR—, —C(O)—, and —NR— to form —NRC(O)NR— (a urea).

Unless otherwise specified, if the replacement occurs at the terminal end, the replacement atom is bound to an H on the terminal end. For example, if a methylene unit of —$CH_2CH_2CH_3$ were optionally replaced with —O—, the resulting compound could be —$OCH_2CH_2$, —$CH_2OCH_3$, or —$CH_2CH_2OH$.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention.

Unless otherwise indicated, a substituent can freely rotate around any rotatable bonds. For example, a substituent drawn as

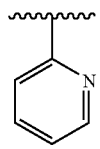

also represents

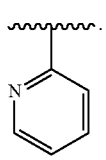

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It will also be appreciated that the compounds of the present invention can exist in free form for treatment, or where appropriate, as a pharmaceutically acceptable salt, salts, or mixtures thereof.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ ($C_{1-4}$alkyl)$_4$ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

In order that this invention be more fully understood, the following preparative examples are set forth. These examples are for the purpose of illustration only and are not to be construed as limiting the scope of the invention in any way.

EXAMPLES

As used herein, the term "HPLC Rt(min)" refers to the HPLC retention time, in minutes, associated with the compound. Unless otherwise indicated, the HPLC method utilized to obtain the reported retention time is as follows:
  Column: ACE C8 column, 4.6×150 mm
  Gradient: 0-100% acetonitrile+methanol 60:40 (20 mM Tris phosphate)
  Flow rate: 1.5 mL/minute
  Detection: 225 nm.

As used herein, the term "LCMS Rt(min)" refers to the LCMS retention time, in minutes, associated with the compound. Mass spec. samples are analyzed on a MicroMass Quattro Micro mass spectrometer operated in single MS mode with electrospray ionization. Samples are introduced into the mass spectrometer using chromatography. Mobile phase, for all mass spec. analyses consists of 10 mM pH 7 ammonium acetate and a 1:1 acetonitrile-methanol mixture, column gradient conditions are 5%-100% acetonitrile-methanol over 3.5 mins gradient time and 5 mins run time on an ACE C8 3.0×75 mm column. Flow rate is 1.2 ml/min.

Example 1

The overall synthetic scheme for the synthesis of 5-fluoro-1H-pyrazolo[3,4-b]pyridin-3-amine (5) is depicted below.

Scheme V

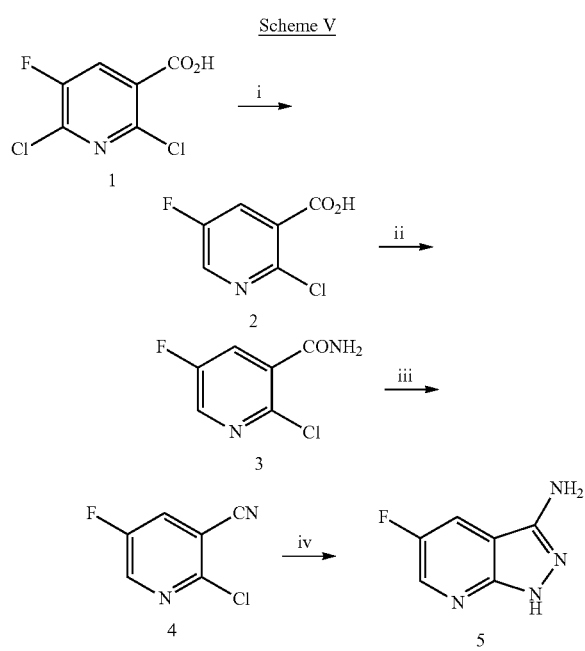

Reagents and conditions: i. Pd(OAc)$_2$, PPh$_3$, Et$_3$N, H$_2$CO$_2$; ii. 1) (COCl)$_2$, CH$_2$Cl$_2$, cat. DMF; 2) NH$_3$ (g), dioxane, iii. TFAA, Et$_3$N, CH$_2$Cl$_2$, 0° C.; iv. H$_2$NNH$_2$·H$_2$O, n-butanol, reflux

2-Chloro-5-fluoronicotinic acid (2)

To a round-bottomed flask under a N$_2$ atmosphere were added degassed DMF (270 mL), Pd(OAc)$_2$ (0.05 eq, 2.7 g, 11.9 mmol), PPh$_3$ (0.1 eq, 6.2 g, 23.8 mmol) and degassed Et$_3$N (6 eq, 200 mL, 1428.6 mmol). The mixture was stirred 20 minutes then HCOOH (3 eq, 28 mL, 714.3 mmol) was added followed after 5 minutes by 2,6-dichloro-5-fluoronicotinic acid (50 g, 238.1 mmol) and the mixture was stirred at 50° C. The reaction was followed by analysis (1H NMR) of a worked-up aliquot. When all starting material was consumed (24 h), the mixture was cooled to 0° C. and water (500 mL) was added. After 20 minutes, The mixture was filtered through a pad of Celite that was rinsed with water. The mixture was basified to pH 9 with 30% aq. NaOH and washed with EtOAc (2×). HCl (12 N) was added slowly to pH 1 and the solution was saturated with NaCl. The mixture was extracted with EtOAc (3×). The combined organic extracts were washed with brine, dried (Na$_2$SO$_4$) and concentrated under reduced pressure to give 37 g (88%) of a beige solid used in the next step without further purification. $^1$H NMR (DMSO-d$_6$, 300 MHz): δ 8.16 (dd, 1H); 8.58 (d, 1H).

2-Chloro-5-fluoronicotinamide (3)

To a solution of 2-chloro-5-fluoronicotinic acid 6 (50 g, 285 mmol) and DMF (2 mL, 28 mmol) in DCM (400 mL) at 0° C. was added oxalyl chloride (64 mL, 741 mmol) dropwise. The reaction mixture was stirred at room temperature overnight and concentrated in vacuo. The resulting yellow liquid was dissolved in 1,4-dioxane (600 mL), cooled at 0° C. and NH$_3$(g) was bubbled through the solution for 30 minutes. The mixture was stirred at room temperature overnight. The resulting mixture was filtered and the filtrate was concentrated to give compound 3 (44 g, 89%) as a beige solid. $^1$H NMR (DMSO-d$_6$, 300 MHz): δ 7.84 (s, 1H), 7.96 (dd, 1H), 8.09 (s, 1H), 8.49 (d, 1H).

2-Chloro-5-fluoronicotinonitrile (4)

A suspension of crude compound 3 (65 g, 372.4 mmol) and Et3N (114 mL, 819.2 mmol) in DCM (700 mL) was cooled to 0° C. and TFAA (57 mL, 409.6 mmol) was added dropwise. The resulting yellow solution was stirred for 90 minutes at 0° C., diluted with DCM, washed with sat. aq. NaHCO$_3$ and brine, and dried (Na$_2$SO$_4$). The mixture was filtered and concentrated. Kugel Rohr distillation of the residue (~70° C./1 mbar) gave 50 g (86%) of compound 4 as a beige solid.

Compound 4 can also be purified by column chromatography (SiO$_2$, 8:1 heptane:EtOAc). $^1$H NMR (CDCl$_3$, 300 MHz): δ 7.78 (dd, 1H); 8.49 (d, 1H).

5-Fluoro-1H-pyrazolo[3,4-b]pyridin-3-amine (5)

To a solution of compound 4 (50 g, 321.7 mmol) in 1-butanol (1 L) was added hydrazine monohydrate (150 mL, 3.2 mol), and the mixture was refluxed for 4 h. The mixture was cooled to room temperature and concentrated. The precipitate was successively washed on filter with water (2×) and Et$_2$O (2×) and dried in vacuo overnight to give compound 5 (44 g, 88%) as a yellow solid. $^1$H NMR (DMSO-d$_6$, 300 MHz): δ 5.53 (s, 2H); 7.94 (dd, 1H); 8.35 (dd, 1H); 12.02 (s, 1H).

The following compounds were made according to Scheme II:

| Cmpd # | | M + 1 (obs) | HPLC Rt (min) | NMR |
|---|---|---|---|---|
| I-1 | 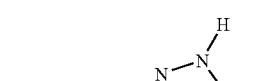 | 396.00 | 9.02 | HNMR (400 MHz, DMSO) 2.31-2.45 (2H, m), 4.00-4.11 (4H, m), 6.80 (1H, s), 7.38-7.60 (4H, m), 8.38-8.45 (1H, m), 8.50-8.58 (1H, m), 10.10 (1H, s), 13.11 (1H, brs). |

-continued
| Cmpd # | | M + 1 (obs) | HPLC Rt (min) | NMR |
|---|---|---|---|---|
| I-2 | 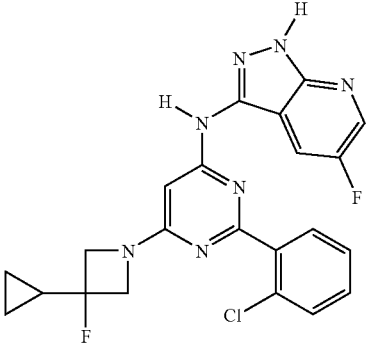 | 454.00 | 9.80 | HNMR (400 MHz, DMSO) 0.39-0.69 (4H, m), 1.37-1.52 (1H, m), 3.89-4.16 (4H, m), 6.35 (1H, brs), 7.38-7.67 (4H, m), 8.34-8.45 (1H, m), 8.51-8.59 (1H, m), 10.24 (1H, s), 13.16 (1H, s). |
| I-4 | 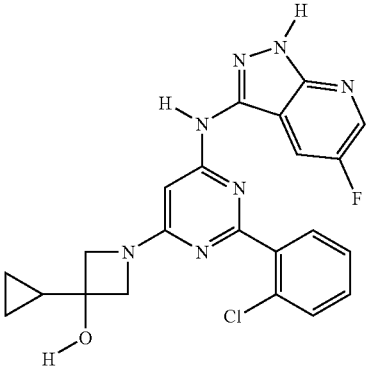 | 452.00 | 8.85 | HNMR (400 MHz, DMSO) 0.25-0.52 (4H, m), 1.13-1.31 91H, m), 3.72-3.94 (4H, m), 5.71 (1H, s), 6.80 (1H, s), 7.33-7.63 (4H, m), 8.28-8.40 (1H, m), 8.49-8.61 (1H, m), 10.16 (1H, s), 13.13 (1H, s). |
| II-1 | 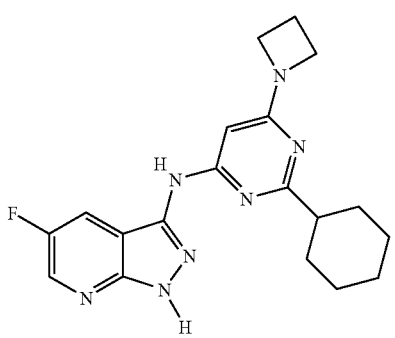 | 368.00 | 3.92 | (400 MHz, DMSO) 1.08-1.92 (10H, m), 2.26-2.58 (3H, m), 3.89-4.06 (4H, m), 6.50 (1H, brs), 8.32-8.62 (2H, m), 9.79 (1H, s), 13.03 (1H, s). |

The following compounds were made according to Scheme I:

| Cmpd # | | M + 1 (obs) | LCMS Rt (min) | NMR |
|---|---|---|---|---|
| III-1 | [structure: 5-fluoro-1H-pyrazolo[3,4-b]pyridin-3-yl amino linked to 6-chloro-2-cyclohexylpyrimidin-4-yl] | 347 | 3.92 | (400 MHz, DMSO) 1.10-1.96 (10H, m), 2.56-2.69 (1H, m), 7.65 (1H, brs), 8.27-8.39 (1H, m), 8.58 (1H, s), 10.72 (1H, s), 13.34 (1H, s). |
| III-3 | [structure: 5-fluoro-1H-pyrazolo[3,4-b]pyridin-3-yl amino linked to 5,6-dimethyl-2-cyclohexylpyrimidin-4-yl] | 341.57 | 3.63 | (DMSO) 0.87-1.22 (5H, m), 1.40-1-62 (5H, m), 2.04 (3H, s), 2.20 (3H, s), 2.25 (1H, quin), 7.67 (1H, dd), 8.40 (1H, dd), 8.91 (1H, s), 13.13 (1H, s). |
| III-4 | [structure: 5-fluoro-1H-pyrazolo[3,4-b]pyridin-3-yl amino linked to 6-methyl-2-(4,4-difluorocyclohexyl)pyrimidin-4-yl] | 363 | 3.42 | (400 MHz, DMSO) 1.77-2.14 (8H, m), 2.35 (3H, s), 2.75-2.87 (1H, m), 7.41 (1H, brs), 8.26-8.38 (1H, m), 8.52-8.62 (1H, m), 10.22 (1H, s), 13.22 (1H, s). |
| III-5 | [structure: 5-fluoro-1H-pyrazolo[3,4-b]pyridin-3-yl amino linked to 5,6-dimethyl-2-(tetrahydro-2H-pyran-4-yl)pyrimidin-4-yl] | 343 | 2.98 | (400 MHz, DMSO) 1.44-1.67 (4H, m), 2.18 (3H, s), 2.35 (3H, s), 2.59-2.70 (1H, m), 3.22-3.37 (2H, m), 3.71-3.82 (2H, m), 7.73-7.83 (1H, m), 8.52-8.59 (1H, m), 9.10 (1H, s), 13.33 (1H, s). |

-continued

| Cmpd # | Structure | M + 1 (obs) | LCMS Rt (min) | NMR |
|---|---|---|---|---|
| III-7 | | 299 | 3.17 | (400 MHz, DMSO) 1.74-1.86 (1H, m), 1.91-2.05 (1H, m), 2.16-2.27 (2H, m), 2.30-2.43 (5H, m), 3.49-3.62 (1H, m), 7.38 (1H, brs), 8.30-8.41 (1H, m), 8.52-8.62 (1H, m), 10.24 (1H, s), 13.20 (1H, s). |
| III-8 | | 341 | 3.73 | (400 MHz, DMSO) 1.38-1.81 (10H, m), 1.85-1.97 (1H, m), 2.33 (3H, s), 2.73-2.84 (1H, m), 7.25-7.41 (1H, m), 8.29-8.38 (1H, m), 8.49-8.60 (1H, m), 10.11 (1H, s), 13.15 (1H, s). |
| III-9 | | 313 | 3.32 | (400 MHz, DMSO) 1.52-2.00 (8H, m), 2.33 (3H, s), 3.04-3.16 (1H, m), 7.36 (1H, brs), 8.25-8.41 (1H, m), 8.49-8.62 (1H, m), 10.17 (1H, s), 13.19 (1H, s). |
| III-10 | | 327.4 | 1.72 | H NMR (500 MHz, MeOD) 8.54 (s, 1H), 8.22 (s, 1H), 2.80 (m, 1H), 1.9-1.1 (m, 10H) |

| Cmpd # | | M + 1 (obs) | LCMS Rt (min) | NMR |
|---|---|---|---|---|
| III-16 | (structure) | 355 | 3.75 | (400 MHz, DMSO) 1.26-1.67 (10H, m), 1.71-1.83 (2H, m), 2.18 (3H, s), 2.34 (3H, s), 2.55-2.66 (1H, m), 7.75-7.89 (1H, m), 8.50-8.59 (1H, m), 9.00-9.15 (1H, m), 13.26 (1H, s). |
| III-17 | (structure) | 329 | 2.87 | (400 MHz., DMSO) 1.75-1.85 (4H, m), 2.35 (3H, s), 2.79-2.91 (1H, m), 3.31-3.48 (2H, m), 3.87-3.97 (2H, m), 7.40 (1H, brs), 8.24-8.39 (1H, m), 8.54-8.63 (1H, m), 10.21 (1H, s), 13.22 (1H, s). |
| III-18 | (structure) | 341.4 | 1.79 | H NMR (500 MHz, DMSO-d6) 13.73 (s, H), 8.64 (s, 1H), 8.25 (s, 1H), 1.89-1.1 (m 12, H), 0.85 (d, J = 7.9 Hz, 3H), 0.74 (d, J = 12.7 Hz, 1H). |
| III-19 | (structure) | 379 | 4.01 | (400 MHz, DMSO) 1.63-1.78 (6H, m), 1.84-2.06 (9H, m), 2.34 (3H, s), 7.30 (1H, brs), 8.27-8.39 (1H, m), 8.52-8.62 (1H, m), 10.03 (1H, s), 13.19 (1H, s). |

-continued
| Cmpd # | | M + 1 (obs) | LCMS Rt (min) | NMR |
|---|---|---|---|---|
| III-20 | 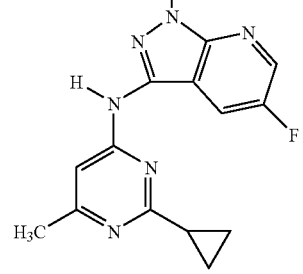 | 285 | 3.03 | (400 MHz, DMSO) 0.88-0.98 (4H, m), 1.94-2.04 (1H, m), 2.30 (3H, s), 7.30 (1H, s), 8.25-8.35 (1H, m), 8.54-8.62 (1H, m), 10.07 (1H, s), 13.17 (1H, s). |
| III-21 | 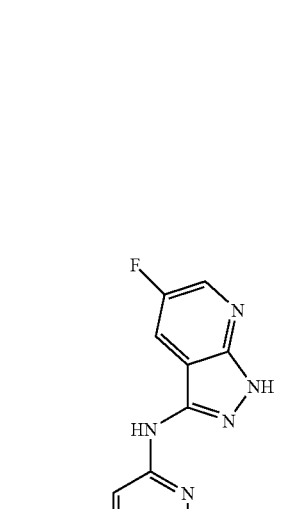 | 371.58 | 3.76 | (DMSO) 1.20-1.39 (3H, m), 1.40 (6H, s), 1.50-1.61 (2H, m), 1.63-1.92 (5H, m), 2.63 (1H, quin), 5.15 (1H, s, OH), 7.14 (1H, br s), 8.33 (1H, dd), 8.56 (1H, dd), 10.12 (1H, s), 13.18 (1H, s). |
The following compounds were made according to Scheme III:
| Cmpd # | | M + 1 (obs) | LCMS Rt (min) | NMR |
|---|---|---|---|---|
| III-23 | | — | — | (DMSO) 7.36 (1H, s), 7.48-7.51 (2H, m), 7.60-7.64 (2H, m), 8.31 (1H, s), 8.43 (1H, d), 8.56 (1H, s), 10.61 (1H, s), 13.17 (1H, s). |

-continued

| Cmpd # | Structure | M + 1 (obs) | LCMS Rt (min) | NMR |
|---|---|---|---|---|
| III-24 | | 368.14 | 3.88 | (DMSO) 1.92 (3H, s), 2.33 (3H, s), 7.37-7.45 (3H, m), 7.55-7.57 (1H, m), 7.82 (1H, s), 8.35 (1H, dd), 8.49 (1H, s), 9.81 (1H, s), 12.86 (1H, s). |
| III-25 | | 354.39 | 3.74 | (DMSO) 2.38 (3H, s), 6.90 (1H, s), 7.42-7.44 (2H, m), 7.53-7.56 (2H, m), 7.75 (1H, s), 8.39-8.41 (1H, m), 8.51 (1H, dd), 9.87 (1H, s), 12.93 (1H, s). |
| III-26 | | 368.25 | 3.93 | (DMSO) 2.26 (3H, s), 2.32 (3H, s), 6.89 (1H, s), 7.27-7.35 (3H, m), 7.45 (1H, d), 7.83 (1H, dd), 8.45 (1H, s), 8.67 (1H, s), 13.07 (1H, s). |
| III-27 | | 334.35 | 3.87 | (DMSO) 2.11 (3H, s), 2.33 (3H, s), 7.40-7.45 (5H, m), 7.78 (1H, s), 8.39 (1H, d), 8.50 (1H, s), 9.71 (1H, s), 12.85 (1H, s). |

The following compounds were made according to Scheme I:

| Cmpd # | Structure | M + 1 (obs) | LCMS Rt (min) | NMR |
|---|---|---|---|---|
| IV-1 | (5-fluoro-1H-pyrazolo[3,4-b]pyridin-3-yl)-[2-(2-chlorophenyl)-5,6-dimethylpyrimidin-4-yl]amine | 369.3 | 1.8 | DMSO d6: 2.28 (3H, s), 2.43 (3H, s), 7.28-7.37 (2H, m), 7.40-7.46 (2H, m), 7.93 (1H, dd), 8.49 (1H, s), 9.28 (1H, br s), 13.39 (1H, br s). |
| IV-2 | (5-fluoro-1H-pyrazolo[3,4-b]pyridin-3-yl)-[2-(2-chlorophenyl)-5-ethyl-6-methylpyrimidin-4-yl]amine | 383.1 | 1.83 | DMSO d6: 1.23 (t, 3H), 2.53 (s, 3H), 2.85 (q, 2H), 7.40 (dd, 1H), 7.45 (dd, 1H), 7.48 (dd, 1H), 7.56 (d, 1H), 7.96 (dd, 1H), 8.51 (s, 1H) |

The following compound was made according to methods described in WO 2004/013140.

| Cmpd # | Structure | M + 1 (obs) | LCMS Rt (min) | NMR |
|---|---|---|---|---|
| V-2 | (5-fluoro-1H-pyrazolo[3,4-b]pyridin-3-yl)-[6-methyl-2-(2-trifluoromethylphenyl)pyrimidin-4-yl]amine | — | 2.15 | H NMR (500 MHz, DMSO-$d_6$) 13.25 (s, 1H), 10.42 (s, 1H), 8.54 (dd, J = 1.5, 2.6 Hz, 1H), 8.29 (dd, J = 2.4, 8.9 Hz, 1H), 7.82-7.58 (m, 5H), 2.42 (s, 3H) |

Compounds of this invention may be tested according to the methods described in WO2004/013140 and WO2002/022607, incorporated herein by reference.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A process for preparing a compound of formula I:

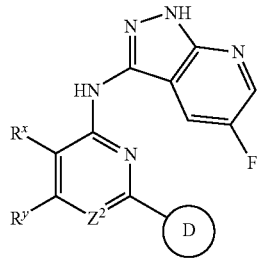

I wherein
$Z^2$ is N or $CR^2$;
$R^x$ is $T^1$-$R^3$;
$R^y$ is $T^2$-$R^{10}$; or
$R^x$ and $R^y$ are taken together with their intervening atoms to form a fused aromatic or non-aromatic 5-8 membered ring having 0-3 ring heteroatoms selected from oxygen, sulfur, or nitrogen, wherein any substitutable carbon on said fused ring formed by $R^x$ and $R^y$ is substituted by T-$R^3$, and any substitutable nitrogen on said ring formed by $R^x$ and $R^y$ is substituted by $R^4$;
$R^z$ is H, halo, or $C_{1-6}$ aliphatic, wherein the aliphatic is optionally substituted with 1-5 groups selected from halo, —CN, and —OR;
each T and $T^1$ is independently a bond or a $C_{1-4}$ alkylidene chain;
$T^2$ is independently a bond or a $C_{1-4}$ alkylidene chain wherein up to three methylene units of the alkylidene chain are optionally replaced by —O—, —C(=O)—, —S(O)—, —S(O)$_2$—, —S—, or —N($R^4$)—;
Ring D is a 4-7 membered monocyclic ring or 8-10 membered bicyclic ring selected from a heterocyclyl, aryl, heteroaryl, or carbocyclyl ring; said heterocyclyl or heteroaryl ring having 1-4 ring heteroatoms selected from nitrogen, oxygen or sulfur, wherein each substitutable ring carbon of Ring D is independently substituted with oxo, $R^1$, or —$R^5$ and any substitutable ring nitrogen is independently substituted with —$R^4$;
$R^1$ is selected from -halo, —CN, —NO$_2$, T-V—$R^6$, phenyl, 5-6 membered heteroaryl ring, 5-6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring D;
V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;
each $R^3$ and $R^{10}$ is independently selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$R", —N($R^4$)N($R^4$)$_2$, —N($R^7$)CON($R^7$)$_2$, —N($R^7$)SO$_2$N($R^7$)$_2$, —N($R^4$)SO$_2$R, or —OC(=O)N($R^7$)$_2$;
each R is independently selected from hydrogen or an optionally substituted group selected from $C_{1-6}$ aliphatic, $C_{6-10}$ aryl, a heteroaryl ring having 5-10 ring atoms, or a heterocyclyl ring having 4-10 ring atoms; each R is optionally substituted with 0-5 $R^9$ or J;
each $R^4$ is independently selected from —$R^7$, —COR$^7$, —CO$_2$R", —CON($R^7$)$_2$, or —SO$_2$R$^7$, or two $R^4$ on the same nitrogen are taken together to form a 3-8 membered heterocyclyl or heteroaryl ring; wherein said heterocyclyl or heteroaryl ring is optionally substituted by 0-3 $J^4$;
each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$R", —N($R^4$)N($R^4$)$_2$, —C(=NH)N($R^4$)$_2$, —C(=NH)—OR, —N($R^4$)CON($R^4$)$_2$, —N($R^4$)SO$_2$N($R^4$)$_2$, —N($R^4$)SO$_2$R, or —OC(=O)N($R^4$)$_2$;
each $R^6$ is independently selected from hydrogen or $C_{1-4}$ aliphatic group optionally substituted with 0-3 $J^6$; or two $R^6$ groups on the same nitrogen atom are taken together with the nitrogen atom to form a 5-6 membered heterocyclyl or heteroaryl ring, wherein said heterocyclyl or heteroaryl ring is optionally substituted with 0-4 $J^6$;
each $R^7$ is independently selected from hydrogen or R"; or two $R^7$ on the same nitrogen are taken together with the nitrogen to form a 5-8 membered heterocyclyl or heteroaryl ring, wherein said heterocyclyl or heteroaryl ring is optionally substituted with 0-4 J";
each $R^8$ is independently selected from —OR$^6$, —SR$^6$, —COR$^6$, —SO$_2$R$^6$, —N($R^6$)$_2$, —N($R^6$)N($R^6$)$_2$, —CN, —NO$_2$, —CON($R^6$)$_2$, —CO$_2$R$^6$, or a $C_{1-4}$ aliphatic group, wherein said $C_{1-4}$ aliphatic group is optionally substituted with 0-3 $J^8$;
each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N(R')$_2$, —OC(=O)R', —N(R')COR', —N(R')CO$_2$(C$_{1-6}$ aliphatic), —N(R')N(R')$_2$, —N(R')CON(R')$_2$, —N(R')SO$_2$N(R')$_2$, —N(R') SO$_2$R', —OC(=O)N(R')$_2$, =NN(R')$_2$, =N—OR', or =O;
each R' is independently hydrogen or a $C_{1-6}$ aliphatic group optionally substituted with 0-4 J'; or two R', together with the atom(s) to which they are attached, form a 3-6 membered carbocyclyl or heterocyclyl wherein said carbocyclyl or heterocyclyl is optionally substituted with 0-4 J' and wherein said heterocyclyl contains 1-2 heteroatoms selected from O, N, or S;
each R" is independently $C_{1-6}$ aliphatic optionally substituted with 0-4 J"; and
each $J^4$, J', and J" is independently NH$_2$, NH($C_{1-4}$ aliphatic), N($C_{1-4}$ aliphatic)$_2$, halogen, $C_{1-4}$ aliphatic, OH, O($C_{1-4}$aliphatic), $NO_2$, CN, $CO_2H$, $CO_2$($C_{1-4}$aliphatic), O(halo$C_{1-4}$ aliphatic), or halo$C_{1-4}$aliphatic;

each J is halo, OH, or $C_{1-6}$aliphatic;

each $J^6$ and $J^8$ is independently -halo, —OR, oxo, $C_{1-6}$ aliphatic, —C(=O)R, —$CO_2R$, —COCOR, $COCH_2COR$, —$NO_2$, —CN, —S(O)R, —S(O)$_2R$, —SR, —N($R^4$)$_2$, —CON($R^7$)$_2$, —$SO_2N(R^7)_2$, —OC(=O)R, —N($R^7$)COR, —N($R^7$)$CO_2$($C_{1-6}$ aliphatic), —N($R^4$)N($R^4$)$_2$, =NN($R^4$)$_2$, =N—OR, —N($R^7$)CON($R^7$)$_2$, —N($R^7$)$SO_2N(R^7)_2$, —N($R^4$)$SO_2R$, or —OC(=O)N($R^7$)$_2$; or 2 $J^6$ or $J^8$ groups, on the same atom or on different atoms, together with the atom(s) to which they are bound, form a 3-8 membered saturated, partially saturated, or unsaturated ring having 0-2 heteroatoms selected from O, N, or S;

comprising the steps of:

1) synthesizing a compound of formula 5

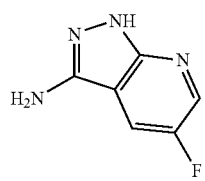

5 comprising the steps of selectively de-chlorinating a compound of formula 1:

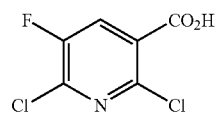

1 under suitable de-chlorination conditions to form a compound of formula 2:

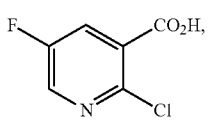

2

2) combining said compound of formula 5 with a compound of formula 6:

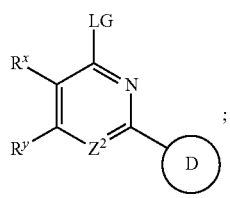

wherein LG is a suitable leaving group; and $R^x$, $R^y$, $Z^2$, and Ring D are as defined herein for compounds of formula I; under suitable reaction conditions to form a compound of formula I.

2. The process of claim 1, wherein said Ring D has one or two ortho substituents independently selected from —$R^1$, any substitutable non-ortho carbon position on Ring D is independently substituted by —$R^5$.

3. The process of claim 1 or claim 2, wherein said compound of formula I is selected from one of the following formulae:

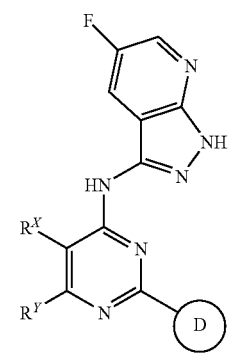

A-1

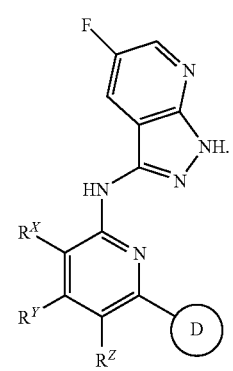

B-1

4. The process of claim 1, wherein LG is F, Cl, Br, I, $C_6$arylsulfonyloxy, $C_{1-4}$alkylsulfonyloxy, trifluoromethanesulfonyloxy, $C_{1-6}$alkylsulfonyl, or $C_{1-6}$alkyl sulfoxide.

5. The process of claim 4, wherein LG is F, Cl, Br, or I.

6. The process of claim 5, wherein LG is chloro.

7. The process of claim 1, wherein Ring D is a 5-10 membered carbocyclyl or a 5-10 membered heterocyclyl where said heterocyclyl contains 1-2 heteroatoms selected from O, N, or S; wherein the carbocyclyl or heterocyclyl is optionally substituted with 1-5 —$R^5$.

8. The process of claim 7, wherein Ring D is a 5-10 membered carbocyclyl.

9. The process of claim 8, wherein Ring D is cyclohexyl.

10. The process of claim 1, wherein Ring D is a 5-7 membered monocyclic aryl or heteroaryl ring, said heteroaryl ring having 1-4 ring heteroatoms selected from nitrogen, oxygen or sulfur.

11. The process of claim 10, wherein Ring D is phenyl or pyridinyl.

12. The process of claim 11, wherein Ring D is phenyl.

13. The process of claim 11, wherein Ring D has one or two ortho substituents independently selected from —$R^1$; and any substitutable non-ortho carbon position on Ring D is independently substituted with —$R^5$.

14. The process of claim 13, wherein Ring D has one ortho substituent selected from —$R^1$.

15. The process of claim 13 or claim 14, wherein $R^1$ is -halo, —CN, or a $C_{1-4}$ aliphatic group optionally substituted with halogen.

16. The process of claim 15, wherein $R^1$ is Cl and $R^5$ is hydrogen.

17. The process of claim 1, wherein $R^X$ is hydrogen, $C_{1-4}$aliphatic, or halo.

18. The process of claim 17, wherein $R^x$ is methyl.

19. The process of claim 1, wherein $R^y$ is $C_{1-4}$ alkyl.

20. The process of claim 19, wherein $R^y$ is methyl.

21. The process of claim 1, wherein $R^y$ is

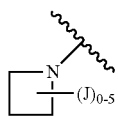

22. The process of claim 1, wherein $R^X$ is hydrogen or $C_{1-4}$aliphatic;

$R^Y$ is

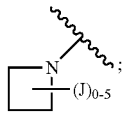

$C_{1-4}$ alkyl optionally substituted with 0-2 J; or a 6 membered heterocyclyl containing 1-2 heteroatoms selected from O, N, or S;

J is halo, OH, or $C_{1-4}$aliphatic;

Ring D is phenyl, $C_{3-10}$ cycloalkyl, or 5-7 membered heterocyclyl containing 1-2 heteroatoms selected from O, N, or S; and $R^1$ is $C_{1-4}$alkyl, $CF_3$, or halo.

23. The process of claim 1, wherein $R^X$ is hydrogen, methyl, or ethyl;

$R^Y$ is

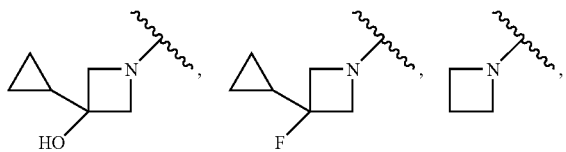

methyl, $CF_3$, Cl, morpholinyl, or $C(CH_3)_2OH$;

Ring D is phenyl, tetrahydro-2H-pyran, adamantyl, cyclopropyl, cyclobutyl, cyclopentyl, cyclohexyl, or cycloheptyl;

$R^1$ is methyl, $CF_3$, or halo; and $R^5$ is H.

24. The process of claim 1, wherein $R^X$ is hydrogen or methyl;

$R^Y$ is methyl;

Ring D is phenyl or cyclohexyl;

$R^1$ is methyl, $CF_3$, or Cl; and $R^5$ is H.

25. The process of claim 1, wherein said compound of formula I is selected from the following:

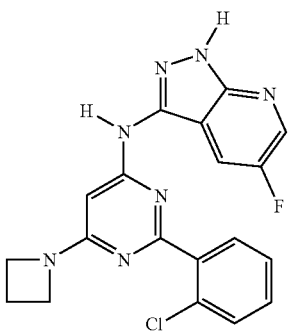

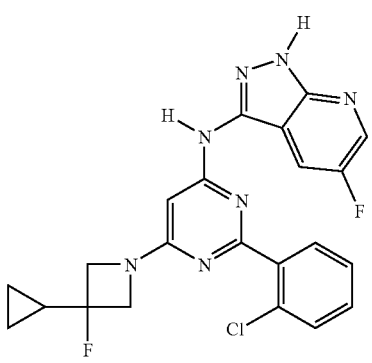

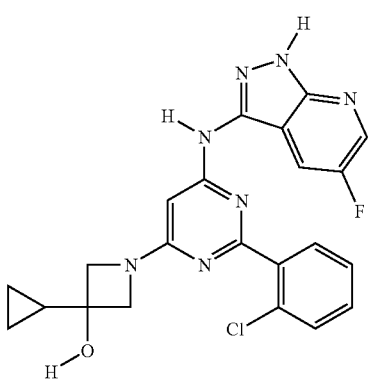

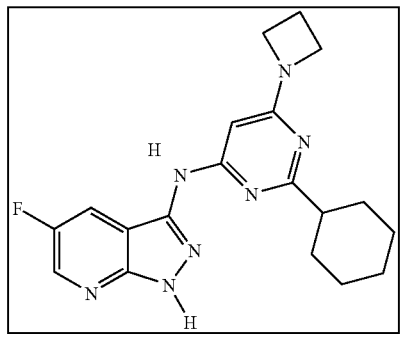

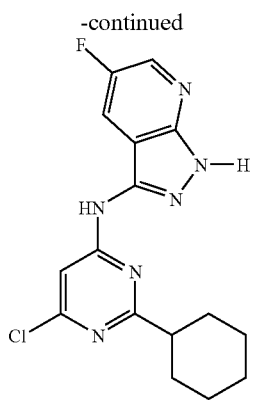
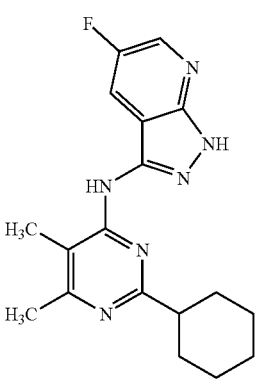
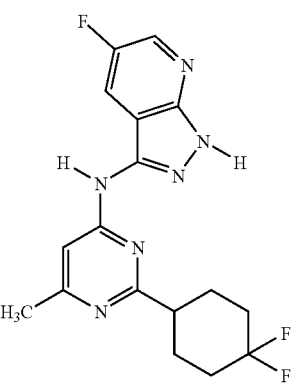
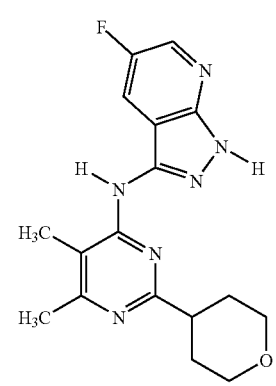
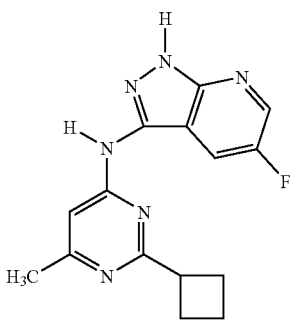
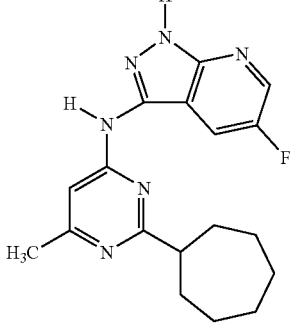
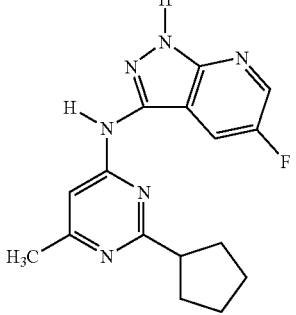
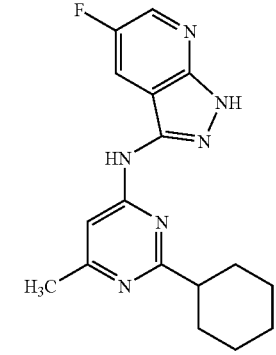
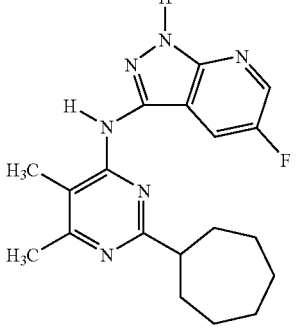

-continued
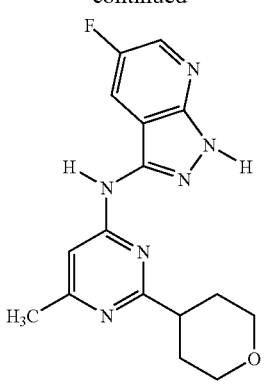
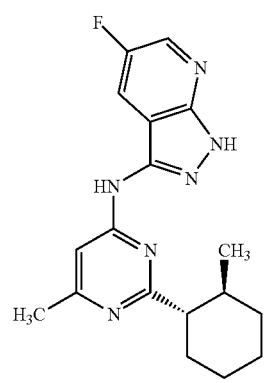
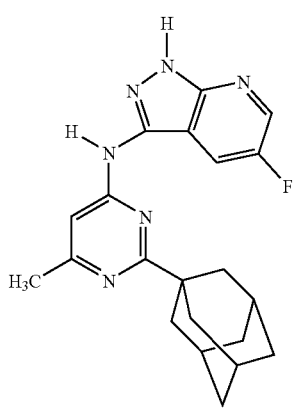
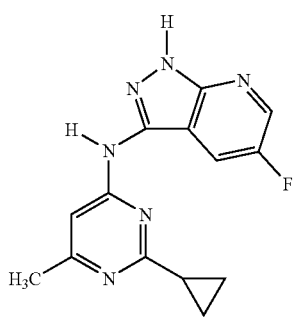
-continued
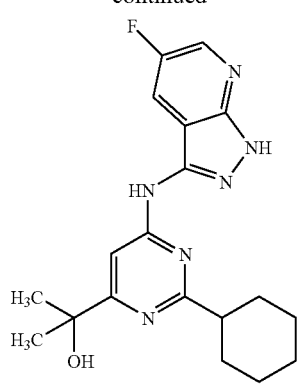
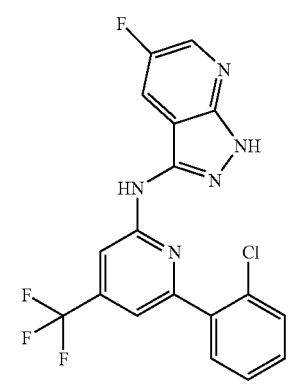
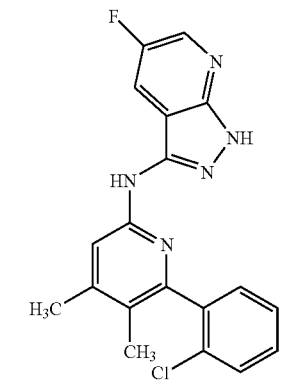
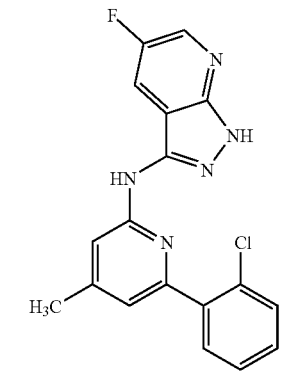

49
-continued
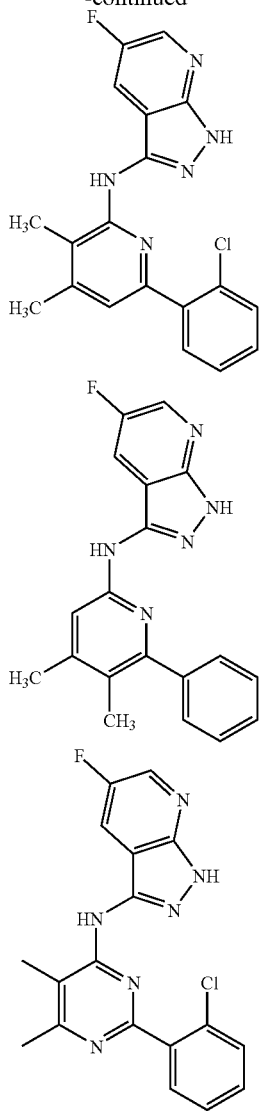
50
-continued
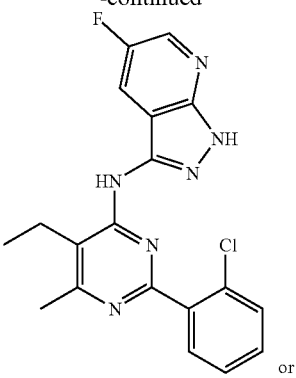
or
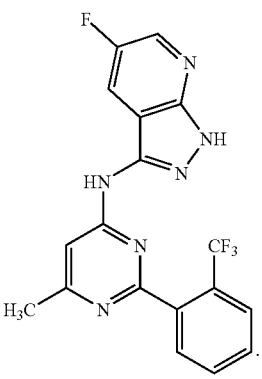
* * * * *